(12) United States Patent
Giacometti et al.

(10) Patent No.: US 12,404,086 B2
(45) Date of Patent: Sep. 2, 2025

(54) LIMITING ACCELERATION OF A MEDICAL DEVICE DROPPED TO THE LOCATION OF AN EMERGENCY MEDICAL EVENT

(71) Applicant: ZOLL Medical Corporation, Chelmsford, MA (US)

(72) Inventors: Paolo Giacometti, North Grafton, MA (US); Gideon Butler, Portsmouth, NH (US); George Reilly, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 876 days.

(21) Appl. No.: 17/505,423

(22) Filed: Oct. 19, 2021

(65) Prior Publication Data

US 2022/0118267 A1    Apr. 21, 2022

Related U.S. Application Data

(60) Provisional application No. 63/093,561, filed on Oct. 19, 2020.

(51) Int. Cl.
| | |
|---|---|
| *B65D 81/02* | (2006.01) |
| *A61N 1/372* | (2006.01) |
| *A61N 1/39* | (2006.01) |
| *B64D 1/12* | (2006.01) |
| *B64D 1/14* | (2006.01) |
| *B65D 27/00* | (2006.01) |
| *B64U 101/57* | (2023.01) |

(52) U.S. Cl.
CPC ....... *B65D 81/022* (2013.01); *A61N 1/37282* (2013.01); *A61N 1/3904* (2017.08); *A61N 1/3968* (2013.01); *A61N 1/3993* (2013.01); *B64D 1/12* (2013.01); *B64D 1/14* (2013.01); *B65D 27/00* (2013.01); *B65D 81/02* (2013.01); *B64U 2101/57* (2023.01)

(58) Field of Classification Search
CPC ...... B64D 1/14; B65D 81/022; B65D 81/052; B62J 27/20; A41D 13/018; B60R 21/36; B60R 2021/0013; B60R 2021/0088; B60R 2021/138
See application file for complete search history.

(56) References Cited

U.S. PATENT DOCUMENTS 2,776,808 A * 1/1957 Vonderahe ............... B64D 1/14
                                                         220/326
5,217,131 A * 6/1993 Andrews .............. B65D 81/052
                                                           383/3

(Continued)

*Primary Examiner* — Michael H Wang
(74) *Attorney, Agent, or Firm* — Finch & Maloney PLLC

(57) ABSTRACT

In an illustrative embodiment, systems and apparatus for limiting acceleration of medical equipment dropped to a location of an emergency medical event include one or more protection elements for protecting the medical equipment against impact forces that may damage the equipment. The protection elements may include one or more elements configured to reduce acceleration of the medical equipment while dropping to the location. The protection elements may include one or more elements configured to absorb impact forces to reduce the forces realized by the medical equipment. The medical equipment may be dropped to the location by an unmanned aerial vehicle.

31 Claims, 25 Drawing Sheets

(56) References Cited

U.S. PATENT DOCUMENTS

| | | | | |
|---|---|---|---|---|
| 5,301,902 | A * | 4/1994 | Kalberer | B64D 25/02 |
| | | | | 280/730.2 |
| 5,812,188 | A * | 9/1998 | Adair | A61B 1/00048 |
| | | | | 600/101 |
| 6,237,875 | B1 * | 5/2001 | Menne | B64D 1/14 |
| | | | | 244/100 A |
| 8,948,935 | B1 * | 2/2015 | Peeters | B64D 1/22 |
| | | | | 709/201 |
| 9,307,383 | B1 | 4/2016 | Patrick | |
| 9,849,979 | B2 | 12/2017 | Peeters et al. | |
| 10,106,257 | B2 * | 10/2018 | Patrick | B64U 10/14 |
| 10,137,986 | B1 * | 11/2018 | Bar-Zeev | B65D 81/03 |
| 10,427,788 | B1 * | 10/2019 | Grenga | B64D 1/14 |
| 10,745,130 | B2 * | 8/2020 | Potter | B64D 1/14 |
| 2015/0069185 | A1 * | 3/2015 | Parkinson | B64D 1/14 |
| | | | | 244/137.3 |
| 2016/0130001 | A1 * | 5/2016 | Cook | B64D 17/26 |
| | | | | 244/145 |
| 2017/0252571 | A1 * | 9/2017 | Dascoli | A61N 1/39044 |
| 2019/0175928 | A1 * | 6/2019 | Christmas | A61N 1/3968 |

* cited by examiner

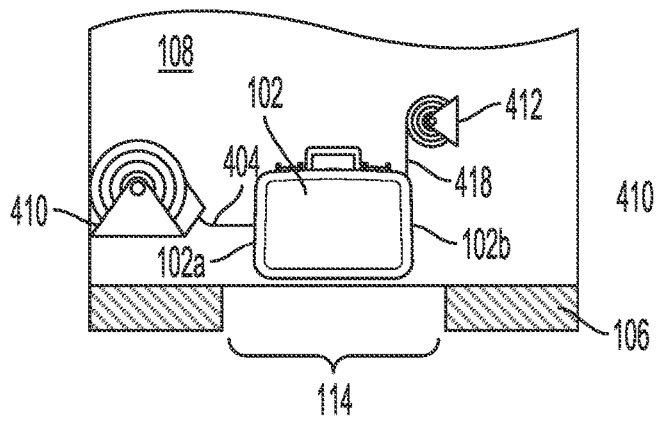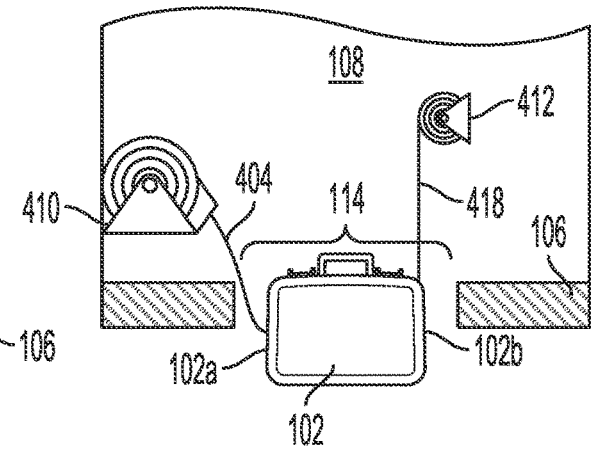
FIG. 4A          FIG. 4B
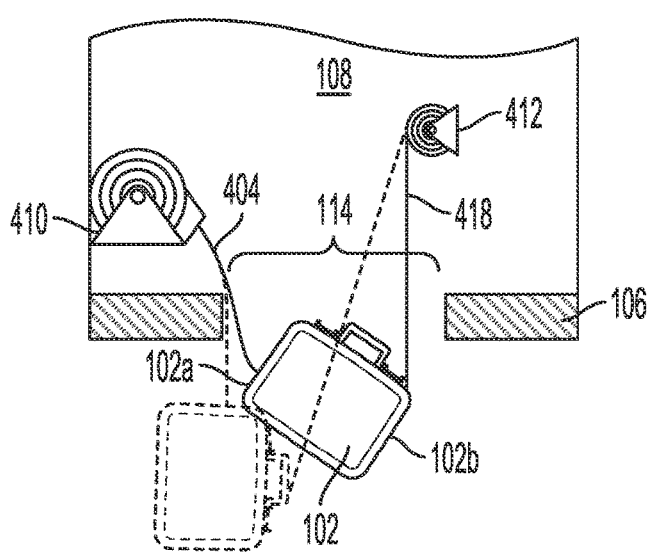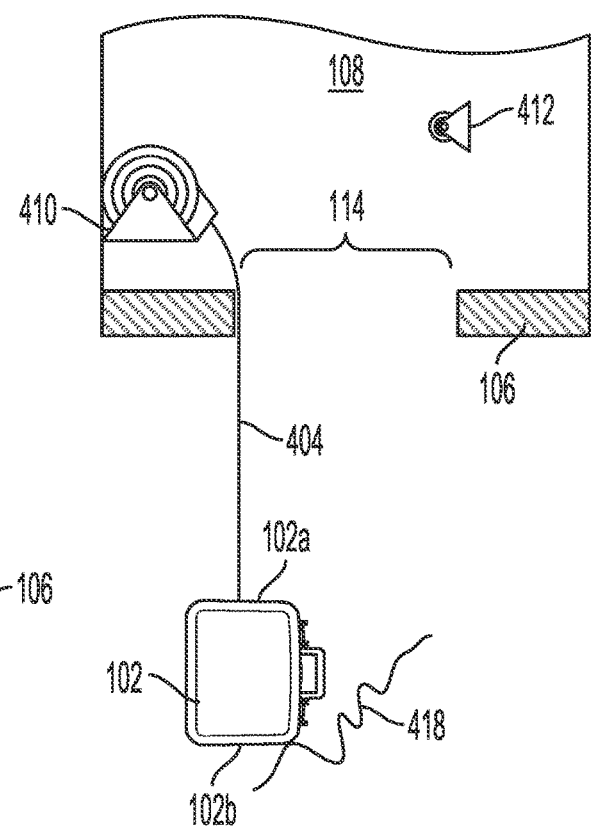
FIG. 4C          FIG. 4D

LIMITING ACCELERATION OF A MEDICAL DEVICE DROPPED TO THE LOCATION OF AN EMERGENCY MEDICAL EVENT

RELATED APPLICATIONS

This application claims priority to U.S. Provisional Patent Application Ser. No. 63/093,561 filed Oct. 19, 2020. The above identified applications are each hereby incorporated by reference in its entirety.

BACKGROUND

Circumstances arise where a victim requires emergency medical help, but emergency medical personnel are incapable of driving to the location or otherwise reaching the location in adequate time to provide necessary medical intervention. This can happen, in some examples, when an elderly person suffers cardiac arrest while shoveling snow and the street has not yet been plowed, when an accident occurs during a hike or other hard-to-reach outdoor location, when a crowd impedes travel of medical personnel (e.g., festival, beach, etc.), or when a major event such as a flood or earthquake impedes emergency personnel mobility. Additionally, because every minute that passes after a patient's heart has stopped corresponds to a significant reduction in odds of complete recovery, many more situations can arise where it is essential to get medical equipment to the scene of an emergency event prior to the fastest possible route that could be taken by emergency personnel, even if only a layperson is there who can be guided through its use.

SUMMARY OF ILLUSTRATIVE EMBODIMENTS

In one aspect, the present disclosure relates to an apparatus for limiting force of impact on a medical device dropped to a location of an emergency medical event, the apparatus including an external case at least partially surrounding or integrated with the medical device, and at least one impact dampening element coupled to the external case, the at least one impact dampening element being configured to transform from a stowed state to a deployed state while the medical device is dropped to the location, where in the stowed state, the at least one impact dampening element is in a compact form, and in the deployed state, the at least one impact dampening element expands to buffer the force acting on the medical device upon impact at the location.

In some embodiments, when in the compact form, the at least one impact dampening element is configured to add less than one centimeter to each side of at least one side of the external case. When in the deployed state, the at least one impact dampening element may expand to add at least 5 centimeters to each side of at least one side of the external case. Each impact dampening element of the at least one impact dampening element may be releasably coupled to the external case by at least one quick release connector. The at least one quick release connector may include hook and loop material, a locking rail and slide, a buckle, or a rotating lock connector.

In some embodiments, the external case is a housing of the medical device. The external case may be a stretchable sleeve or envelope. The external case may include a flexible material surrounding the medical device and secured to the medical device with at least one closure element designed for quick removal of the case at the location of the emergency medical event. The at least one closure element may include a hook and loop material, a zipper, a buckle, or a snap.

In some embodiments, the external case includes rigid material surrounding the medical device and secured to the medical device with at least one closure element designed for quick removal of the case at the location of the emergency medical event. The at least one closure element may include a hook and loop material, a zipper, a buckle, or a snap.

In some embodiments, the stowed state is a compressed state and the deployed state is an expanded state. The stowed state may be a deflated state and the deployed state may be an inflated state. The at least one impact dampening element may include an airbag.

In some embodiments, transforming from the stowed state to the deployed state includes holding, when dropping the medical device to the location, a pull cord configured to activate inflation of the at least one impact dampening element and to release from the external case when pulled. Transforming from the stowed state to the deployed state may include activating inflation by igniting a propellant. Transforming from the stowed state to the deployed state may include activating inflation by releasing a compressed gas.

In some embodiments, transforming from the stowed state to the deployed state includes activating inflation through a signal delivered by processing circuitry. The processing circuitry may be configured to monitor sensor signals indicative of gravitational force (g-force), and responsive to detecting at least a threshold g-force, activating inflation of the at least one impact dampening element. The medical device may include the processing circuitry.

In some embodiments, transforming from the stowed state to the deployed state includes selectively inflating a portion of the at least one impact dampening element corresponding to a downward pointing side of the external case. Selectively inflating may include analyzing one or more sensor signals to identify the downward pointing side of the external case. The one or more sensor signals may be provided by a sensor built into the medical device. Selectively inflating may include opening an inflation valve responsive to detecting flow direction of a liquid switch mechanism. The medical device may include the liquid switch mechanism. The liquid switch mechanism may be disposed between the external case and an internal housing of the medical device. The liquid component may include mercury. The liquid component may include a low-density liquid portion and a high-density liquid portion configured to remain separated from the low-density liquid portion. The high-density liquid portion may include an oil. The low-density liquid portion may include water.

In some embodiments, the apparatus is designed for being dropped to the location by an aerial delivery vehicle, and holding the pull cord includes securing the pull cord to a surface of a payload region of the aerial delivery vehicle such that the pull cord is held within the aerial delivery vehicle.

In some embodiments, the at least one impact dampening element includes at least one spring. The at least one spring may be arranged along at least four sides of the external case. The coils of the at least one spring may be sized to extend across and beyond two edges of a side of the external case. The at least on spring may be a wire spring, a metal spring, or a plastic spring.

In some embodiments, the at least one impact dampening element includes at least two telescoping members configured to extend outwards from the external case in the deployed state. The at least two telescoping members may include a spring release to transform from the stowed state to the deployed state. The at least two telescoping members may include a pneumatic release to transform from the stowed state to the deployed state.

In some embodiments, the at least one impact dampening element is disposed on a side of the external case corresponding to a heaviest side of the medical device. The at least one impact dampening element may be disposed on a side of the external case closest to one or more components of the medical device having a lowest impact rating. The at least one impact dampening element may be disposed on a side of the external case corresponding to a direction of impact force likely to loosen or dislodge one or more components of the medical device. The at least one impact dampening element may be configured to limit a force of impact on the medical device dropped from a height of about 10 feet to no more than 2 g-force impact upon landing on the at least one impact dampening element.

In one aspect, the present disclosure relates to an enclosure for limiting force of impact on a medical device dropped to a location of an emergency medical event, the enclosure including a three-dimensional shell including at least two sections, where a first section of the at least two sections is at least partially releasable from a second section of the at least two sections for positioning medical equipment in the three-dimensional shell, a number of airbag units including a first portion of airbag units disposed on a first section of the three-dimensional shell, and a second portion of airbag units disposed on a second section of the three-dimensional shell, at least one source of inflation material for inflating the number of airbag units, and a trigger mechanism for causing inflation of at least a portion of the number of airbag units with material from the at least one source of inflation.

In some embodiments, the first section is hingedly attached to the second section. The three-dimensional shell may include a viewing area for viewing a display of the medical device while the medical device is enclosed in the three-dimensional shell. The viewing area may include an opening in the three-dimensional shell.

In some embodiments, the three-dimensional shell includes a number of openings for accessing a number of input/output features of the medical device while the medical device is enclosed in the three-dimensional shell. The number of airbag units may be arranged upon the three-dimensional shell such that the input/output features remain accessible while all airbag units of the number of airbag units are in an inflated state.

In some embodiments, the three-dimensional shell includes an access port for accessing an extension of the medical device. The extension may include one of electrode leads of a defibrillation medical device, an oxygen mask and delivery hose of a ventilation medical device, or a biometric monitoring unit. The biometric monitoring unit may be a blood oxygen sensor, a heart rate monitor, or a blood pressure monitor.

In some embodiments, the three-dimensional shell includes a descent line connection feature for connecting a descent line to the enclosure. The descent line connection feature may include an opening for connecting one of the descent line or a descender unit to the enclosure. The the three-dimensional shell may include a handle configured to enable a user to carry the medical device within the three-dimensional shell.

In some embodiments, the three-dimensional shell includes a number of attachment features for releasably attaching the number of airbag units. The number of attachment features may include a number of slots, each slot of the number of slots being configured to releasably receive at least one connector for fixing an airbag unit of the number of airbag units to the respective slot. Each airbag unit of the number of airbag units may include an airbag and an attachment substrate, where the attachment substrate is configured for releasable attachment to at least one attachment feature of the three-dimensional shell. The attachment substrate may include at least one mounting bracket for mounting the airbag unit to a given attachment feature of the number of attachment features of the three-dimensional shell. The mounting bracket may be configured to releasably receive a connector. The connector may include one of a bolt, a screw, a nut, or a snap connector. The attachment substrate may be configured for wrapping around a corner or an edge of the three-dimensional shell. The attachment substrate may be flexible. The attachment substrate may be substantially composed of a plastic, a silicon, a felt material, a fiber, or a corrugated material. Each airbag unit of the number of airbag units may be configured for releasable replacement, after inflation of the respective airbag unit, with a new airbag unit.

In some embodiments, the enclosure includes at least one motion or directional sensor, where the trigger is configured to activate release of the material from the at least one source of inflation based on signals provided by the at least one motion or directional sensor. The enclosure may include a manifold for directing the material from the at least one source of inflation to each airbag unit of the number of airbag units. The enclosure may include selection circuitry for selectively engaging at least a portion of a number of output feeds of the manifold. The selection circuitry may selectively engage the portion of the number of output feeds responsive to estimating an area of impact upon the three-dimensional shell. Estimating the area of impact may include determining, using the signals provided by the at least one motion or directional sensor, an orientation of the enclosure.

In one aspect, the present disclosure relates to an apparatus for limiting force of impact on a medical device dropped to a location of an emergency medical event, the apparatus including an external case at least partially surrounding or integrated with the medical device, where the external case includes a first connection element of a connector pair disposed on a surface of the external case, and at least one shock absorbing element including a second connection element of the connector pair such that the at least one shock absorbing element is releasably coupled to the external case by the connector pair, where the connector pair is configured for simple release at the location by effort of a rescuer without use of a tool. The at least one shock absorbing element, when coupled to the external case, may be configured to limit a force of impact on the medical device dropped from a height of about 10 feet to no more than 2 g-force impact upon landing on the at least one shock absorbing element.

In some embodiments, a first element of the at least one shock absorbing element is a shock absorption cushion. The shock absorption cushion may include a gel material, a foam material, or a rubber material. A first element of the at least one shock absorbing element may be a crushable shock absorption element configured to crumple upon impact. The crushable shock absorption element may include a cardboard material, a paper material, a metal material, a plastic material, or a wood material. The connector pair may include hook and loop material, a locking rail and slide, a buckle, or a rotating lock connector.

In one aspect, the present disclosure relates to a medical device configured to be dropped to a location of an emergency medical event, the medical device including a set of defibrillation electrodes, and a housing enclosing a circuit board including control circuitry, a capacitor mounted to the circuit board, where the capacitor is configured to produce a defibrillation shock delivered via the defibrillation electrodes, an inflatable protection element disposed proximate to an electronic element mounted to the circuit board, and a sensor configured for collecting signals for measuring g-force. The control circuitry may be configured to analyze the signals to detect a threshold g-force or greater, and responsive to detecting the threshold g-force, cause inflation of the inflatable protection element.

In some embodiments, the electronic element is the capacitor, and the inflatable protection element is toroidal and encircles at least a portion of the capacitor. The electronic element may be a communication unit configured to enable wireless communication between the control circuitry and an external computing device. The communication unit may enable at least one of Wi-Fi communication or Bluetooth communication. The inflatable protection element may encircle at least a portion of the communication unit.

In some embodiments, the medical device is an Automated External Defibrillator (AED). The inflatable protection element may be an airbag. The me inflatable protection element may be configured to automatically deflate after the medical device has reached the location.

In some embodiments, the control circuitry is configured to analyze further signals to detect a second threshold g-force smaller than the threshold g-force, and responsive to detecting the second threshold g-force, cause the inflatable protection element to deflate. The second threshold g-force may be zero g-force. The threshold g-force may be 2 g.

In some embodiments, causing inflation of the inflatable protection element includes igniting a propellant. Causing inflation of the inflatable protection element may include releasing a compressed gas. The compressed gas may be carbon dioxide. The inflatable protection element may be reusable.

In one aspect, the present disclosure relates to an apparatus for limiting force of impact on a medical device dropped to a location of an emergency medical event, the apparatus including an external case at least partially surrounding or integrated with the medical device, and one or more air diverting elements coupled to one or more sides of the external case, where the one or more air diverting elements are configured to align an orientation of the medical device while the medical device is dropping to the location.

In some embodiments, the one or more air diverting elements are configured to generate drag while the medical device is dropping to the location, thereby slowing descent of the medical device. The one or more air diverting elements may include a pair of air diverting elements disposed on opposing parallel surfaces of the external case.

In some embodiments, the one or more air diverting elements includes a number of fins. The number of fins may be disposed in an orientation opposite the direction of air flow during descent of the medical device. Disposing the number of fins may include arranging the number of fins pointed in a direction of a top or a bottom of the medical device. The bottom of the medical device may be heavier than the top of the medical device. A descent line coupled to the medical device may initially orient the medical device while dropping to the location.

In some embodiments, the one or more air diverting elements includes a number of funnel-shaped air diverting elements disposed in an orientation such that the direction of air flow during descent of the medical device moves from a wider section of the funnel shape to a narrower section of the funnel shape. The one or more air diverting elements may include a parachute. A canopy of the parachute may include a number of openings. The canopy may include a mesh material. The canopy may include a net material. The canopy of the parachute may be generally round. The canopy of the parachute may be generally rectangular. The canopy of the parachute may include a central opening disposed at a top of the canopy. The canopy of the parachute may be tethered to the external case proximate four corners of a top of the medical device. The canopy of the parachute may be tethered to a handle of the external case. The parachute may be configured to deploy upon releasing the medical device from an aerial delivery vehicle.

In one aspect, the present disclosure relates to a system for limiting acceleration of medical equipment dropped to a location of an emergency medical event, the system including an external case at least partially surrounding or integrated with the medical equipment, and a descender unit fixed to one of i) the medical equipment or ii) the external case, the descender unit being configured to provide a travel path for a descent line, where at least one of the descent line and the descender unit are configured to reduce acceleration of the medical equipment as the medical equipment travels downward along the descent line by applying frictional force to the descent line.

In some embodiments, the descent line includes a rolled or folded sheet of material. Layers of the rolled or folded sheet may resist separation due to static friction. The rolled or folded sheet of material may include rubber. The descender unit may include a rotating component, where the descent line feeds around the rotating component. The descent line may be looped around the component and secured with a sliding knot. The rotating component may include a number of fins, where air flow against the number of fins asserts a counter-rotational force against the rotating component.

In some embodiments, the system includes a second descent line, and a second descender unit including a second rotating component, where the second descent line feeds around the second rotating component, and the descender unit and the second descender unit are disposed on parallel opposing sides of the external case. The descender unit may include a surface treatment configured to increase frictional force between the descender unit and the descent line.

In some embodiments, the descender unit includes a loop having a central opening and at least two protrusions each extending from the loop in a respective direction opposite the central opening, and the descender unit is configured to receive the descent line in an over-under wrap around the loop, where the at least two protrusions are configured to prevent a first side of the descent line from contacting a second side of the descent line. The descender unit may include a pair of rigid members separated by two extensions, where each pair of extensions of the at least two extensions are separated by gap at least the width of the descent line such that the descender unit is configured for feeding the descent line around the at least two extensions in an "S" path. The at least two extensions may include two textured pins.

In some embodiments, the descender unit includes a clamp for clamping the descent line to the medical device and frictionally feeding the descent line through the clamp. The descender unit may include an adjustable connector for selecting one of a number of resistance settings to apply to the descent line. The adjustable connector may include at least one bolt for manually setting a variable resistance.

In some embodiments, the descender unit includes a housing including an upper side, a lower wall, and two opposing side walls, and an upper opening in the upper wall and a lower opening in the lower wall for feeding the descent line through the housing, and a number of extensions including at least one extension protruding from each wall of the two opposing side walls, where a first extension protruding from a first side wall of the two opposing side walls is disposed parallel and vertically offset from a second extension protruding from a second side wall of the two opposing side walls, and each extension of the at least one extension extends from the corresponding side wall to at least a center of a width between the two opposing side walls, such that the descent line, in feeding through the housing, is fed in an S-shaped path past each extension of the number of extensions, whereby ends of the number of extensions apply frictional force to the descent line as the descent line feeds through the housing. The housing may include a number of openings including at least one opening in each side wall of the two opposing side walls, and the number of extensions may each protrude through the respective opening of a number of openings into the housing. A depth of protrusion of each extension of the number of extensions into the housing may be selectable. Each extension of the number of extensions may screw into the housing such that the depth of protrusion is variable based on a length of threads of each extension screwed through the respective side wall of the housing. Each extension of the number of extensions may include at least two holes to selectively receive a connector for attaching the respective extension to the housing. The connector may be a nut and bolt. The number of extensions may be spring-loaded extensions, such that the extensions exert a horizontal force against the descent line as the descent line feeds through the housing.

In some embodiments, the descender unit includes a housing including an upper side and a lower side, and an upper opening in the upper side and a lower opening in the lower side for feeding the descent line through the housing, and one or more rotatable features disposed within the housing, where the one or more rotatable features apply a rotational counter force to the motion of the descent line as the descent line feeds through the housing. The housing may include at least one vertical side extending between the upper side and the lower side, and at least one of the one or more rotatable features is mounted to a first vertical side of the at least one vertical side. A first rotatable feature of the one or more rotatable features may apply the rotational counter force to the motion of the descent line by pressing the descent line against an inner surface of the housing. The descender unit may include two rotatable features, and the two rotatable features may apply the rotational counter force to the motion of the descent line by pressing the descent line between the two rotatable features. The two rotatable features may function as opposing cams. The one or more rotatable features may include a series of at least three convex surfaces for applying the rotational counter force to the motion of the descent line. The one or more rotatable features may include at least three concave surfaces between the at least three convex surfaces. Applying the rotational counter force to the motion of the descent line may include pushing the descent line into a curved path.

In one aspect, the present disclosure relates to a descent line for limiting acceleration of medical equipment dropped to a location of an emergency medical event, the descent line including a series of sliding knots configured to slideably extend, thereby increasing a length of the descent line, when pulled by the weight of an apparatus hanging from an end of the descent line. The descent line may include a number of links releasably connecting sets of sliding knots of the number of sliding knots, where each link of the number of links is configured to release when pulled by the weight of the apparatus. The number of links may be a number of lengths of material tying the sets of sliding knots together. The material may be string. Slideably extending may include releasing the series of sliding knots. Slideably extending may include tightening the series of sliding knots.

In one aspect, the present disclosure relates to a system for limiting acceleration of a medical device dropped to a location of an emergency medical event, the system including a medical equipment deployment unit for aerial delivery, a descent line, an aerial delivery vehicle, and a descent line feeder unit configured for releasing the descent line. At least one of the descent line or the descent line feeder unit may be configured to reduce acceleration of the medical equipment deployment unit as the medical equipment deployment unit travels downward from the aerial delivery vehicle along the descent line. The aerial delivery vehicle may be configured to, when positioned above the location of the emergency medical event with the descent line attached to the descent line feeder unit and attached to the medical equipment deployment unit, release the medical equipment deployment unit to drop along the descent line at least partway to a ground surface at the location of the emergency medical event. In some embodiments, the medical device is an Automated External Defibrillator (AED) or a trauma kit.

In some embodiments, the aerial delivery vehicle includes a payload region internal to the aerial delivery vehicle and configured to receive the medical equipment deployment unit, and a hatch disposed on a bottom surface of the aerial delivery vehicle and defining a bottom surface of the payload region. The descent line feeder unit may be fixed to a surface of the payload region.

In some embodiments, the medical equipment deployment unit includes a medical device, and a frame, case, or harness releasably coupled to and at least partially surrounding the medical device. The medical equipment deployment unit may include additional equipment, where the frame, case, or harness at least partially surrounds both the medical device and the additional equipment. The additional equipment may include at least one of a trauma kit or a communication device.

The system may include a descender unit fixed to the medical equipment deployment unit, the descender unit being configured to provide a travel path for the descent line. The descent line feeder unit may be fixed to a surface of the aerial delivery vehicle.

In some embodiments, the system includes a delivery apparatus for enclosing the medical equipment deployment unit during transit to the location by the unmanned aerial vehicle, where the descent line feeder unit is fixed to a surface of the delivery apparatus. The delivery apparatus may include a cushioning layer for cushioning impact forces to the medical equipment deployment unit during flight.

In some embodiments, the descent line feeder unit includes a release spool for releasing the descent line. The descent line feeder unit may include a collection reel for collecting the descent line such that, for a portion of the time that the medical equipment deployment unit is being lowered to the location, the medical equipment deployment unit hangs from a length of the descent line between a first end connected to the release spool and a second end connected to the collection reel, where the descent line is collected by the collection reel and removed from the location by the unmanned aerial vehicle. The release spool may include a braking mechanism for controllably releasing the descent line. The descent line feeder unit may include a secondary spool for preventing swinging and/or spinning of the medical equipment deployment unit, where the secondary spool includes a second descent line shorter than the descent line, where the second descent line is connected to a different surface of the medical equipment deployment unit than the descent line. The secondary spool may be configured to release at least a portion of the second descent line prior to the feeder spool releasing the descent line. The secondary spool may fully release the second descent line to travel to the location with the medical equipment deployment unit.

In some embodiments, the descent line feeder unit includes a descender, where the descent line is looped through the descender with a first end of the descent line connected to the medical equipment deployment unit and a second end of the descent line spooled within a cargo region integrated into or carried by the unmanned aerial vehicle. The second end of the descent line may be configured to release from the unmanned aerial vehicle prior to the medical equipment deployment unit. The second end of the descent line may be configured to be longer than a drop height for releasing the medical equipment deployment unit such that the second end of the descent line reaches the ground prior to the medical equipment deployment unit.

In some embodiments, the descent line feeder unit includes a descender, where the descent line is looped through the descender and through a descender unit attached to the medical equipment deployment unit. The medical equipment deployment unit may be disposed within a cargo region integrated into or carried by the unmanned aerial vehicle. A first end of the descent line may be disposed beneath the medical equipment deployment unit in the cargo region. A second end of the descent line may be disposed on top of the medical equipment deployment unit in the cargo region. Upon release of the medical equipment deployment unit by the unmanned aerial delivery vehicle, the first end of the descent line may drop toward the location, and the second end of the descent line may feed through the descender and the descender unit, thereby providing a belaying effect that reduces acceleration of the medical equipment deployment unit toward the location. The second end of the descent line may be attached to the medical equipment deployment unit.

The foregoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 4A through FIG. 4D illustrate a first example descent slowing apparatus including a pair of descent lines for limiting acceleration of a medical device dropped to the location of an emergency medical event;

DETAILED DESCRIPTION OF ILLUSTRATIVE EMBODIMENTS

Figure 1B:
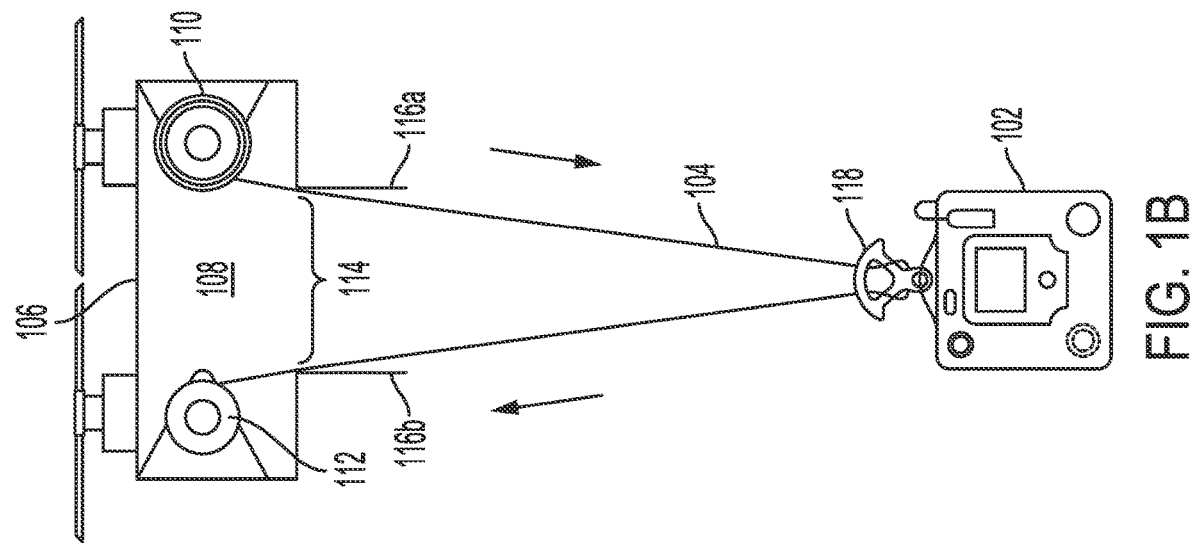
FIG. 1A through FIG. 1C illustrate a first example descent slowing apparatus including a descent line for limiting acceleration of a medical device dropped to the location of an emergency medical event.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that feature or function may be deployed, utilized or implemented in connection with the alternative embodiment unless the feature or function is incompatible with the alternative embodiment.

The inventors recognized an opportunity, if a rescuer is on hand, to deliver emergency medical equipment to provide immediate support to a victim by dropping equipment to the location of a health emergency. The inventors recognized the need for solutions to ensure expensive and complex medical equipment are gently delivered to a location to avoid damage. Further, the inventors recognized the need for providing a failsafe mechanism in the event that a primary mechanism for controlled delivery fails. For example, equipment may be dropped using an unmanned aerial vehicle (UAV) or drone. Delivery drones are used to deliver packages, both commercially and in military situations. The drones typically deliver lightweight (e.g., up to about five pounds) packages. In other examples, equipment may be dropped via helicopter, over the edge of a cliff or precipice, or off of the side of a structure.

To avoid damage to emergency medical equipment, such as an Automated External Defibrillator (AED), a trauma kit, an aspirator, a portable ventilator, or a physiological monitoring and assistance prompting device for remote medical support, the inventors have devised apparatus and methods for limiting acceleration of the emergency medical equipment while being dropped from the aerial delivery vehicle to a location of the emergency medical event and for dampening the force of impact when the emergency medical equipment reaches the ground. The apparatus for slowing acceleration and/or dampening impact force is generally referred to herein as protection elements. Certain protection elements, in some embodiments, can be coupled directly to the medical equipment. In some embodiments, at least a portion of the protection elements are configured for coupling or fixing to a frame, case, cage, or harness at least partially surrounding the emergency medical device. When the emergency medical device or equipment set is coupled with one or more protection elements and otherwise readied for stowing in the aerial delivery vehicle (e.g., coupled to a cage, frame, case, or harness), the bundled package is referred to herein as a medical equipment deployment unit.

In some embodiments, the protection elements may be configured to reduce the force of impact to no more than 2 g-force based on a drop height of about ten feet. In other examples, the force of impact may be no more than about 2.5 g-force at a height between ten feet and fifteen feet, or from a drop height of between fifteen feet and thirty feet. Combinations of protection elements may be provided to enable this reduction in impact force. For example, for a first portion of delivery, a descent line protection element may controllably lower the device (e.g., to within no more than ten feet of the ground, to within five to ten feet of the ground, etc.), while during a second portion of delivery (e.g., free fall), impact dampening elements may reduce the force of impact upon landing at the location.

In some implementations, the protection elements are configured to limit acceleration of the medical equipment deployment unit to a threshold acceleration level when performing a drop anticipated to be performed at a target distance from the surface. Each medical device or bundle of medical equipment, for example, may be rated through quality assurance testing to a maximum acceleration level to avoid damage. The threshold acceleration level, therefore, should be set to no greater than the maximum acceleration level and is preferably set to a lower acceleration level in case of unique circumstances such as uneven ground creating a greater potential for damaging impact than experienced in the quality assurance testing lab and/or to account for the added weight of certain protection elements, in some examples. The threshold acceleration level, in some examples, may be less than 50 g-forces, about 40 g-forces, about 30 g-forces, or under 25 g-forces. The anticipated distance, in some examples, may be about 15 feet, about 20 feet, about 30 feet, or up to 50 feet from the ground. Correspondingly, a length of time for the medical equipment deployment unit to reach the ground may vary based upon the distance, threshold acceleration level, and weight of the medical equipment deployment unit 102. However, it is preferable for the length of time to be as short as safely possible to provide the accident victim or patient with the needed help as soon as possible. Thus, it is anticipated that, in many embodiments, the length of time of descent will be under 10 seconds or around 3-5 seconds. Swift delivery, additionally, may avoid potential imbalances in the medical equipment deployment unit 102 as it is deployed, for example due to wind effects. In certain embodiments including the use of descent lines, this may improve the ability of the aerial delivery vehicle to adjust for forces applied to the aerial delivery vehicle by the dangling medical equipment deployment unit 102. In embodiments involving free fall, this may encourage landing on a preferred side of the medical equipment deployment unit 102 and/or avoid impact on a corner of the medical equipment deployment unit 102, potentially leading to tumbling of the medical equipment deployment unit 102 and impacts on other surfaces that may be more susceptible to damage.

To place the accident victim or patient in a position for best chance of survival, it is preferred to design the protection elements for easy release and/or positioning that leaves controls, connection, and tools available for immediate use by the rescuer. For example, a cage, case, harness, or frame is preferably designed for easy removal or easy access to the medical equipment through the cage, case, harness, or frame. Further, to enable transport in the aerial delivery vehicle, the protection elements are preferably fairly light weight and streamlined in design to fit into a payload region of the aerial delivery vehicle.

In the event of a medical equipment drop involving an aerial delivery vehicle, in some implementations, a controller assists in directing a drone to a location of an emergency medical event, for example through monitoring cameras and ensuring potential hazards are avoided. Once the aerial delivery vehicle has arrived at the location, the controller may adjust a height of the aerial delivery vehicle above a ground surface and/or select a suitable drop zone lacking potential hazards (e.g., a relatively flat area devoid of debris, people, landscape impediments such as trees or rocks, etc.) and/or presenting an opportunity to minimize potential damage to the medical equipment (e.g., grass rather than asphalt). Once the controller has confirmed the aerial delivery vehicle is in the appropriate position, the controller may trigger release of the medical equipment through opening a hatch at the bottom of the aerial delivery vehicle. In some embodiments, the drone continues descent during release of the medical equipment, for example to accelerate deployment of the medical equipment and/or to minimize the distance from the ground at which the medical equipment is deployed. Deploying the medical equipment from the aerial delivery vehicle, in some embodiments, includes an additional step of triggering a release of a mechanism for controlled descent of the medical equipment, such as selecting a control to engage one or more protection elements for protecting the medical equipment during the drop. The controller may then monitor the release of the medical equipment to ensure successful delivery to the rescuer.

Figure 1A:
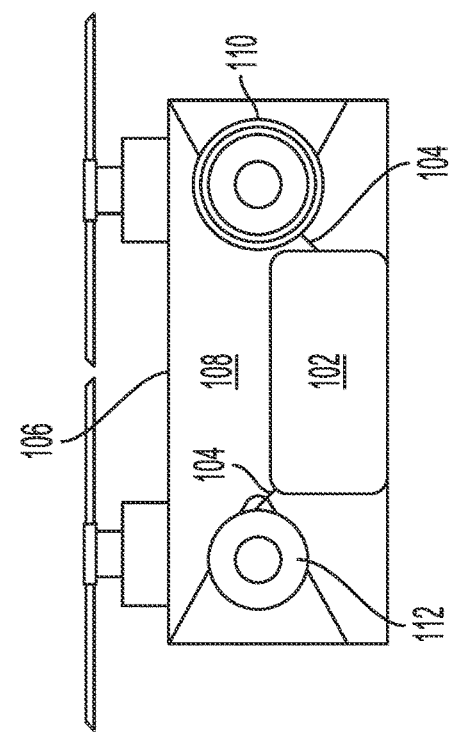
Figure 1C:
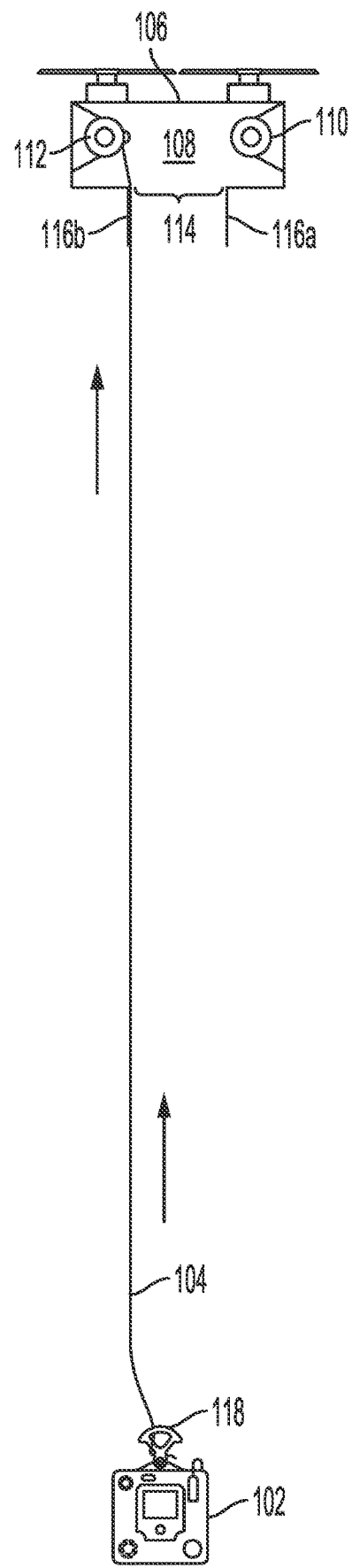

FIG. 1A through FIG. 1C illustrate a first example descent slowing apparatus including a descent line 104 for limiting acceleration of a medical device 102 (e.g., illustrated as an AED device) dropped to the location of an emergency medical event. The medical device 102, for example, may be dropped to the location of the emergency medical event along the descent line 104 to limit the acceleration of the medical device 102 while dropping.

As illustrated in FIG. 1A, in transit, the medical device 102 (e.g., a medical equipment deployment unit) is positioned in within a payload region 108 of an aerial delivery vehicle 106 between a reel 110 and a retractable tether 112. A majority of the descent line 104 is wound around the reel 110 while the medical equipment deployment unit 102 is being delivered to the location of the emergency medical event.

In some implementations, the reel 110 and the retractable tether 112 are fixed to sides of the payload region 108 of the aerial delivery vehicle 106. For example, the reel 110 and the retractable tether 112 may be bolted, welded, or otherwise fixedly secured to side walls of the payload region 108 of the aerial delivery vehicle 106. In other implementations (not illustrated), the reel 110 and the retractable tether 112 are fixed to sides of a delivery crate, cage, or frame enclosing the medical equipment deployment unit 102 and protecting the medical equipment deployment unit 102 while in transit. For example, the delivery crate, cage, or frame may be designed to protect the medical equipment deployment unit 102 against damage due to acceleration events on the aerial delivery vehicle 106, including knocking against or crashing into articles during flight.

The reel 110, in some implementations, is a freely rotating reel of cord, twine, rope, or other line (e.g., fishing type line) forming the descent line 104. In other implementations, the reel 110 is designed with a friction or ratcheting to control feeding the descent line 104 too quickly through the hatch 114. Additionally, in some embodiments, the reel 110 may be designed with a brake that is released by the initial drop of the medical equipment deployment unit 102 (e.g., after opening the hatch 114). In this circumstance, the tension provided by the retractable tether 112 on the descent line 104 will not work to feed the descent line onto the retractable tether 112 during transit to the location of the emergency medical event. Conversely, in some embodiments, the retractable tether 112 may be designed with a brake that is released by the initial drop of the medical equipment deployment unit 102 (e.g., after opening the hatch 114). In a further example, a brake function of one or both of the reel 110 and the retractable tether 112 may be triggered by a control signal sent to the aerial delivery vehicle to cause the hatch 114 to release.

Turning to FIG. 1B, when the aerial delivery vehicle 106 has reached the location, in some implementations, a hatch 114 in the aerial delivery vehicle 106 opens (shown as being covered by a pair of doors 116a, 116b), and the medical equipment deployment unit 102 is deployed. As the medical equipment deployment unit 102 drops to the ground, the descent line 104 unspools from the reel 110 as the g-forces on the medical equipment deployment unit 102 pull the medical equipment deployment unit 102 toward the ground. Additionally, the retractable tether 112 provides a force pulling on an opposite end of the descent line 104, allowing gravity to draw the descent line through a descender 118 connected to the medical device. The descender 118, in some implementations, may take one of the forms of descenders described in relation to FIG. 6A through FIG. 6C. The friction of the descent line 104 drawing through the descender 118 in this manner limits the acceleration of the medical equipment deployment unit 102 as it travels toward the ground.

Turning to FIG. 1C, in some embodiments, the retractable tether 112 continues to wind the descent line 104 within the payload region 108 of the aerial delivery vehicle 106, collecting the descent line 104 after the medical equipment deployment unit 102 has reached the ground. In this manner, in some examples, the rescuer is unhindered by the descent line, nothing is left dangling from the aerial delivery vehicle that could potentially be pulled, and the descent line 104 may be reused in deploying another medical equipment deployment unit. Although illustrated, in this embodiment, as reaching the ground with the medical equipment deployment unit 102, in other implementations, the descent line 104 is shorter in length such that a brief free-fall of the medical equipment deployment unit 102 occurs while the retractable tether 112 spools the descent line 104.

Although illustrated with the reel 110 mounted within the payload region 108 of the aerial delivery vehicle 106, in other embodiments (not illustrated), the reel 110 is attached to the medical equipment deployment unit 102. In one example, rather than using the descender 118, the reel itself is used to limit acceleration of the medical equipment deployment unit 102 due to the friction necessary to unwind the descent line 104. Further to the example, the reel 110 may be fitted with a brake to increase friction upon release of the descent line 104. In another example, the descender 118 may be used in addition to a medical equipment deployment unit-mounted reel 110 to increase friction during descent (e.g., rather than or in addition to a braking mechanism in the reel 110). As with the embodiment illustrated in FIGS. 1A through 1C, once the descent line 104 has fully unwound from the reel 110, the retractor 112 would retract it up into the payload region 108 of the aerial delivery vehicle 106, leaving the empty reel 110 behind on the medical equipment deployment unit 102.

FIG. 2A through FIG. 2D illustrate a second example descent slowing apparatus including a descent line 204 for limiting acceleration of the medical device equipment deployment unit 102 when dropped to the location of an emergency medical event.

Figure 2A:
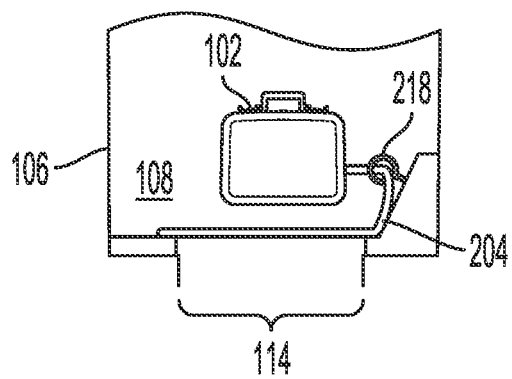
FIG. 2A through FIG. 2D illustrate a second example descent slowing apparatus including a descent line for limiting acceleration of a medical device dropped to the location of an emergency medical event.
Figure 2B:
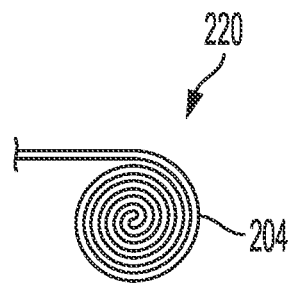

As illustrated in FIG. 2A, in transit, the medical equipment deployment unit 102 is positioned in within the payload region 108 of the aerial delivery vehicle 106. A descent line 204 is fixed to the medical equipment deployment unit 102 and looped through a descender 218. The descender 218, in some implementations, may take one of the forms of descenders described in relation to FIG. 6A through FIG. 6C. The descent line 204 is arranged beneath the medical equipment deployment unit 102 above the hatch 114. For example, the descent line 204 may be arranged beneath the medical equipment deployment unit 102 in a spooled configuration 220, as illustrated in FIG. 2B.

In some implementations, the descent line 204 is fixed to a cage, case, frame, or harness coupled to a medical device as part of the medical equipment deployment unit 102. For example, the descent line 204 may be clipped to a harness or a fixture attached to a cage, case, or frame. In other implementations, the descent line 218 is removably attached to the medical equipment, such as tying the descent line 218 to a handle of a medical device.

In some implementations, the descender 218 is fixed to the side of the payload region 108 of the aerial delivery vehicle 106. For example, the descender 218 may be bolted, welded, or otherwise fixedly secured to a side wall of the payload region 108 of the aerial delivery vehicle 106. In other implementations (not illustrated), the descender 218 is fixed to a side of a delivery crate, cage, or frame enclosing the medical equipment deployment unit 102 and protecting the medical equipment deployment unit 102 while in transit. For example, the delivery crate, cage, or frame may be designed to protect the medical equipment deployment unit 102 against damage due to acceleration events on the aerial delivery vehicle 106, including knocking against or crashing into articles during flight.

Figure 2C:
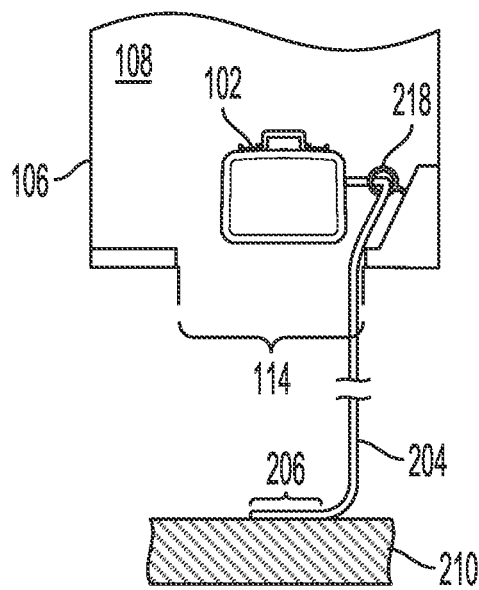

Turning to FIG. 2C, when the aerial delivery vehicle 106 has reached the location, in some implementations, the hatch 114 in the aerial delivery vehicle 106 opens, and the descent line 204 drops through the hatch 114 such that an end 206 of the descent line 204 reaches a ground surface 210 at the location of the emergency medical event. The end 206 of the descent line 204, in some implementations, is weighted to encourage the descent line 204 to quickly reach the ground and/or to increase friction with the ground. For example, by reducing drag against the ground, the end 206 of the descent line 204 may work to anchor the medical equipment deployment unit 102 and reduce the ability of the medical equipment deployment unit 102 to swing (e.g., like a pendulum) during descent. In some implementations, the end 206 of the descent line 204 includes one or more features to increase friction between the end 206 of the descent line and the ground. For example, the end 206 of the descent line 204 may include a roughened or textured surface, such as the surface of a scouring pad or Velcro hooks. In another example, the end 206 of the descent line 204 may include a tacky surface, such as a rubberized surface, gel pad surface, or soft silicone surface. The tacky surface may in turn include a texturized component, such as ridges, bumps, and/or channels to add another frictional component.

Figure 2D:
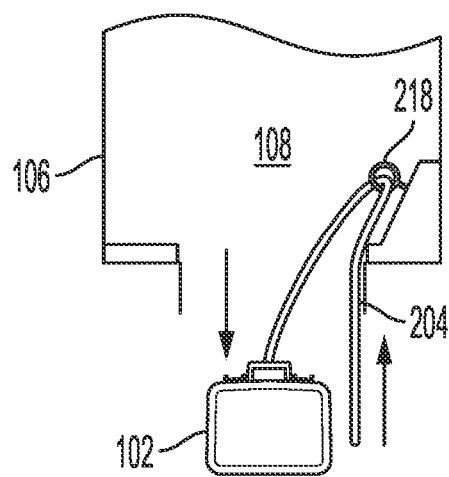

Turning to FIG. 2D, after the descent line 204 drops through the hatch 114, in some implementations, the medical equipment deployment unit 102 drops through the hatch 114, placing downward tension on the descent line 204 and pulling the descent line 204 through the descender 218 while the medical equipment deployment unit 102 travels toward the ground surface 210. The descender 218 applies a frictional force, thereby limiting acceleration of the medical equipment deployment unit 102 as it travels the distance between the hatch 114 and the ground surface 210. Further, the counter force of the majority of the length of the descent line 204 reduces the ability of the medical equipment deployment unit 102 to swing after being dropped from the hatch 114. Depending upon the distance of the drop and/or a length of time of the drop, by avoiding a pendulum swing the aerial delivery device 106 may remain stable during deployment of the medical equipment deployment unit 102.

Once the medical equipment deployment unit 102 has reached the ground surface 210, in some implementations, the descent line 204 continues to travel through the descender 218 (potentially aided by an operator lifting the aerial delivery vehicle 106 to a greater distance from the surface of the ground 210), until the end 206 of the descent line 204 clears the descender 218 and the entire descent line 204 falls to the ground surface 210. Here, the descent line 204 may be discarded or collected for reuse at a later time.

In some implementations, the connection of the descender 218 to the wall of the payload region 108 of the aerial delivery vehicle 106 or another surface and/or a material factor of the descender 218 itself provide a safety breakaway for the descender 218, for example if the descent line 204 is pulled. This further provides safety protection to the aerial delivery vehicle 106.

Figure 3A:
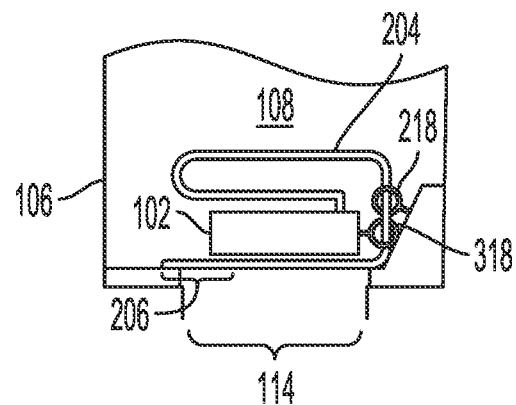
FIG. 3A through FIG. 3C illustrate a third example descent slowing apparatus including a descent line for limiting acceleration of a medical device dropped to the location of an emergency medical event.
Figure 3B:
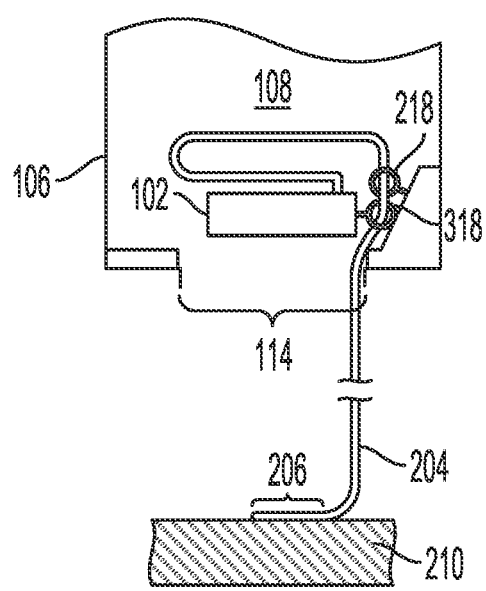
Figure 3C:
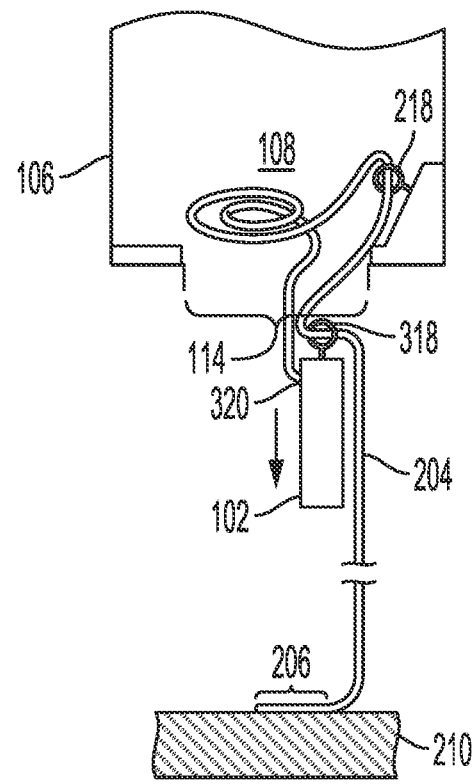

FIG. 3A through FIG. 3C illustrate a third example descent slowing apparatus including a descent line for limiting acceleration of a medical device dropped to the location of an emergency medical event.

Similar to the descent slowing apparatus of FIG. 2A through FIG. 2D, as illustrated in FIG. 3A, in transit, the medical equipment deployment unit 102 is positioned in within the payload region 108 of the aerial delivery vehicle 106. The descent line 204 is fixed to the medical equipment deployment unit 102, for example in a configuration as described above in relation to FIG. 2A through FIG. 2D. However, a first portion of the descent line 204 is arranged on top of the medical equipment deployment unit 102, and a second portion of the descent line 204 including the end 206 is positioned beneath the medical equipment deployment unit 102 and above the hatch 114. As described in relation to FIG. 2B, the each of the portion of the descent line 204 on top of the medical equipment deployment unit 102 and the portion of the descent line 204 beneath the medical equipment deployment unit 102 may be arranged in the spooled configuration 220. Unlike the descent slowing apparatus of FIG. 2A through FIG. 2D, the descent line 204 is looped through both the descender 218, which is attached, for example, as explained in relation to FIG. 2A through FIG. 2D, and a descender 318 fixed to the medical equipment deployment unit 102. The descender 318, in some implementations, may take one of the forms of descenders described in relation to FIG. 6A through FIG. 6C.

In some implementations, the descender 318 is fixed to a cage, case, frame, or harness coupled to a medical device as part of the medical equipment deployment unit 102. In other implementations, the descender 318 is fixed to the medical equipment, such as building the descender 318 into a handle of a medical device or bolting the descender 318 to a surface of the medical device.

Turning to FIG. 3B when the aerial delivery vehicle 106 has reached the location, in some implementations, the hatch 114 in the aerial delivery vehicle 106 opens, and the portion of the descent line 204 arranged beneath the medical equipment deployment unit 102 drops through the hatch 114 such that the end 206 of the descent line 204 reaches the ground surface 210 at the location of the emergency medical event. The end 206 of the descent line 204, in some implementations, is weighted to encourage the end 206 of the descent line 204 to quickly reach the ground and to reduce lateral drag due to friction with the ground. In some embodiments, the hatch 114 may only partially open (e.g., only one door) to allow for the bottom portion of the descent line 204 to drop prior to the medical equipment deployment unit 102.

Turning to FIG. 3C, after the bottom portion of the descent line 204 drops through the hatch 114, in some implementations, the medical equipment deployment unit 102 drops through the hatch 114, placing downward tension on the upper portion of the descent line 204 by a fixed connection 320 to the medical equipment deployment unit 102 which pulls the upper portion of the descent line 204 through the hatch 114. At this time, the descender 218 substantially retains the descent line 204 in position in relation to the portion already deployed to the ground surface. When the upper portion of the descent line 204 is fully deployed through the hatch 114, frictional resistance asserted on the descent line 204 by the descender 218 positioned in the payload region 108 of the aerial delivery vehicle 106 limits acceleration of the medical equipment deployment unit 102 as it travels toward the surface of the ground 210. Further, the counter force of the upper portion of the descent line 204, connected at the connection point 320 to the medical equipment deployment unit 102, works as a pulley to slowly deliver the medical equipment deployment unit 102 to the ground surface 210.

Once the medical equipment deployment unit 102 has reached the ground surface 210, in some implementations, the end 206 of the descent line 204 is significantly closer to the aerial delivery vehicle 106 than to the ground surface 210. A controller of the aerial delivery vehicle 106 may initiate ascent of the aerial delivery vehicle 106 to a greater distance from the surface of the ground 210 until the end 206 of the descent line 204 clears the descender 218 and the entire descent line 204 falls to the ground surface 210. Here, the descent line 204 may be discarded or collected for reuse at a later time.

FIG. 4A through FIG. 4D illustrate a first example descent slowing apparatus including a pair of descent lines for limiting acceleration of a medical device dropped to the location of an emergency medical event.

Turning to FIG. 4A, in some implementations, a primary braking spool 410 and a secondary spool 412 are fixed to sides of the payload region 108 of the aerial delivery vehicle 106. For example, the primary braking spool 410 and the secondary spool 412 may be bolted, welded, or otherwise fixedly secured to side walls of the payload region 108 of the aerial delivery vehicle 106. In other implementations (not illustrated), the primary braking spool 410 and the secondary spool 412 are fixed to sides of a delivery crate, cage, or frame enclosing the medical equipment deployment unit 102 and protecting the medical equipment deployment unit 102 while in transit. For example, the delivery crate, cage, or frame may be designed to protect the medical equipment deployment unit 102 against damage due to acceleration events on the aerial delivery vehicle 106, including knocking against or crashing into articles during flight.

The secondary spool 412, in some implementations, is a freely rotating reel of cord, twine, rope, or other line (e.g., fishing type line) forming a secondary descent line 418. The primary braking spool 410, conversely, is designed with a friction brake or ratcheting to control feeding a primary descent line 404 too quickly through the hatch 114. The primary descent line 404, further, may be formed of a different material (e.g., cord, twine, rope, fishing line, etc.).

The primary descent line 404 is connected proximate a top 102a of the medical equipment deployment unit 102 (e.g., in relation to a descent orientation), and the secondary descent line 418 is connected proximate a bottom 102b of the medical equipment deployment unit 102.

Turning to FIG. 4B, in some implementations, after the hatch 114 of the aerial delivery device 106 has opened, the medical equipment deployment unit 102 begins descent, unspooling both the primary descent line 404 and the secondary descent line 418.

Turning to FIG. 4C, in some implementations, the bottom 102b of the medical equipment deployment unit 102 swings downward due to the lower tension on the secondary descent line 418 by the secondary spool 412 than on the primary descent line 404 by the primary braking spool 410. Meanwhile, the secondary spool 412 and the secondary descent line 418 provide controlled tension to the bottom of the medical equipment deployment unit 102 to allow for controlled deployment, thereby avoiding a pendulum swing of the medical equipment deployment unit 102 on the primary descent line 404.

Turning to FIG. 4D, eventually, the secondary descent line 418 fully unspools from the secondary spool 412, and the medical equipment deployment unit 102 proceeds to descend on the primary descent line 404. The primary descent line 404 may fully unspool during deployment of the medical equipment deployment unit 102, leaving the primary descent line 404 and the secondary descent line 418 on the surface at the location of the emergency medical event.

In other implementations, rather than including the secondary spool 412 and the secondary descent line 418, a braking mechanism of the primary braking spool 410 may be designed to control an initial unspooling of the primary descent line 404 to ensure that only a limited pendulum swing could develop.

FIG. 5A through FIG. 5D illustrate a second example descent slowing apparatus including a pair of descent lines for limiting acceleration of a medical device dropped to the location of an emergency medical event.

Figure 5A:
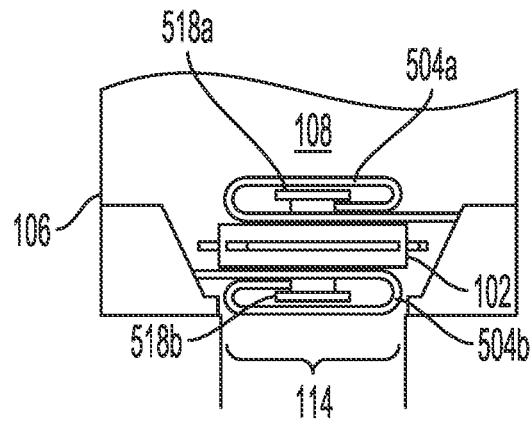
FIG. 5A through FIG. 5D illustrate a second example descent slowing apparatus including a pair of descent lines for limiting acceleration of a medical device dropped to the location of an emergency medical event.

Turning to FIG. 5A, similar to FIG. 3A, in transit, the medical equipment deployment unit 102 is positioned in within the payload region 108 of the aerial delivery vehicle 106 with a first descent line 504a arranged on top of the medical equipment deployment unit 102, and a second descent line 504b positioned beneath the medical equipment deployment unit 102 and above the hatch 114. As described in relation to FIG. 2B, each of the descent line 204a on top of the medical equipment deployment unit 102 and the descent line 204b beneath the medical equipment deployment unit 102 may be arranged in the spooled configuration 220.

In some implementations, each of the first descent line 504a and the second descent line 504b is fixed to a side of the payload region 108 of the aerial delivery vehicle 106. For example, the first descent line 504a and the second descent line 504b may be attached to a connector that is bolted, welded, or otherwise fixedly secured to side walls of the payload region 108 of the aerial delivery vehicle 106. In other implementations (not illustrated), the first descent line 504a and the second descent line 504b are fixed to sides of a delivery crate, cage, or frame enclosing the medical equipment deployment unit 102 and protecting the medical equipment deployment unit 102 while in transit. For example, the delivery crate, cage, or frame may be designed to protect the medical equipment deployment unit 102 against damage due to acceleration events on the aerial delivery vehicle 106, including knocking against or crashing into articles during flight.

Figure 5B:
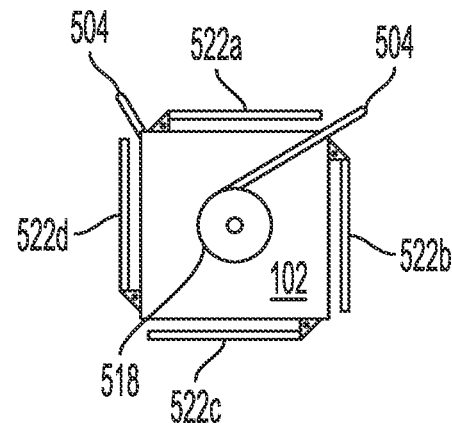

In some implementations, a second end of each of the first descent line 504a and the second descent line 504b is spooled around a corresponding first rotating descender 518a and second rotating descender 518b. Turning to FIG. 5B, each rotating descender 518 is mounted to a front surface or a back surface of the medical equipment deployment unit 102. Four fins 522a-d are each hingedly attached to the four sides of the medical equipment deployment unit 102.

In some implementations, the rotating descenders 518a,b and/or the fins 522a-d are fixed to a cage, case, frame, or harness coupled to a medical device as part of the medical equipment deployment unit 102.

Figure 5C:
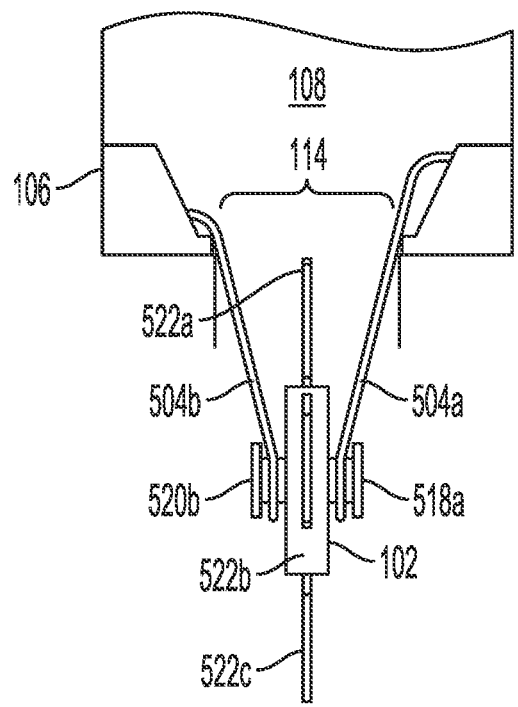

Turning to FIG. 5C, when the aerial delivery vehicle 106 has reached the location of the emergency medical event, in some implementations, the hatch 114 in the aerial delivery vehicle 106 opens, and the medical equipment deployment unit 102 is lowered toward the ground by the first and second descent lines 504a,b unspooling from the rotating descenders 518a,b.

Figure 5D:
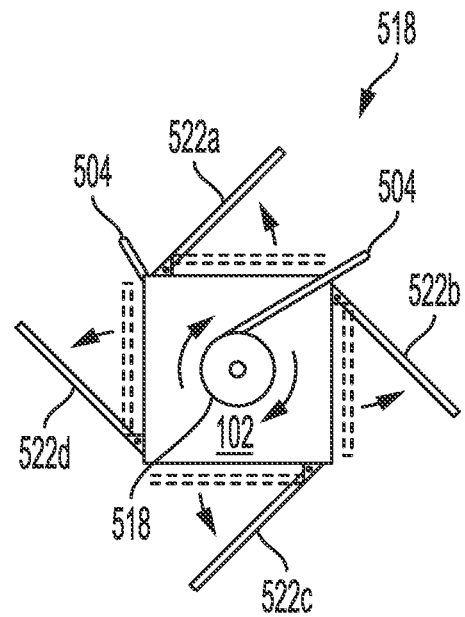

Turning to FIG. 5D, if the medical equipment deployment unit 102 rotates as it is descending, the fins 522a-d hinge open to counter the rotation. The fins 522a-d, in some embodiments, limit acceleration of the medical equipment deployment unit 102 through air resistance. For example, the descent lines 504b, 504a may be designed to generate initial rotation and fin deployment, after which the medical equipment deployment unit 102 free falls to the ground. In some embodiments, the fins 522a-d are designed and/or positioned to encourage maintaining vertical alignment of the medical equipment deployment unit 102 during descent. The fins 522a-d, in some examples, may be designed using light aerodynamic metal, plastic, and/or wood material. In some embodiments, the fins 522a-d are designed as shock absorbers upon reaching the ground surface. For example, the fins may be designed using flexible materials and/or flexible connections (e.g., spring hinges, etc.) to absorb impact of the medical equipment deployment unit 102 contacting the ground surface. In some embodiments, the fins 522a-d are designed for a single use, such that the fins 522a-d may be damaged upon contact with the ground surface. In other embodiments, the fins 522a-d are designed to close upon impact and resist damage so that the fins 522a-d (for example, as attached to a case or frame at least partially surrounding the medical equipment deployment unit 102) may be used for subsequent aerial deployment of medical equipment deployment units.

FIG. 6A through FIG. 6D illustrate various example descender units for releasably connecting a medical device to a descent line. The descender units are configured to allow a descent line to feed through the unit. Different designs may apply different levels of friction or braking resistance to the descent line to assist in slowing the descent of the medical equipment deployment unit to the ground. Further, different designs may provide varying levels of stability and control of the medical equipment deployment unit 102 during descent.

Figure 6A:
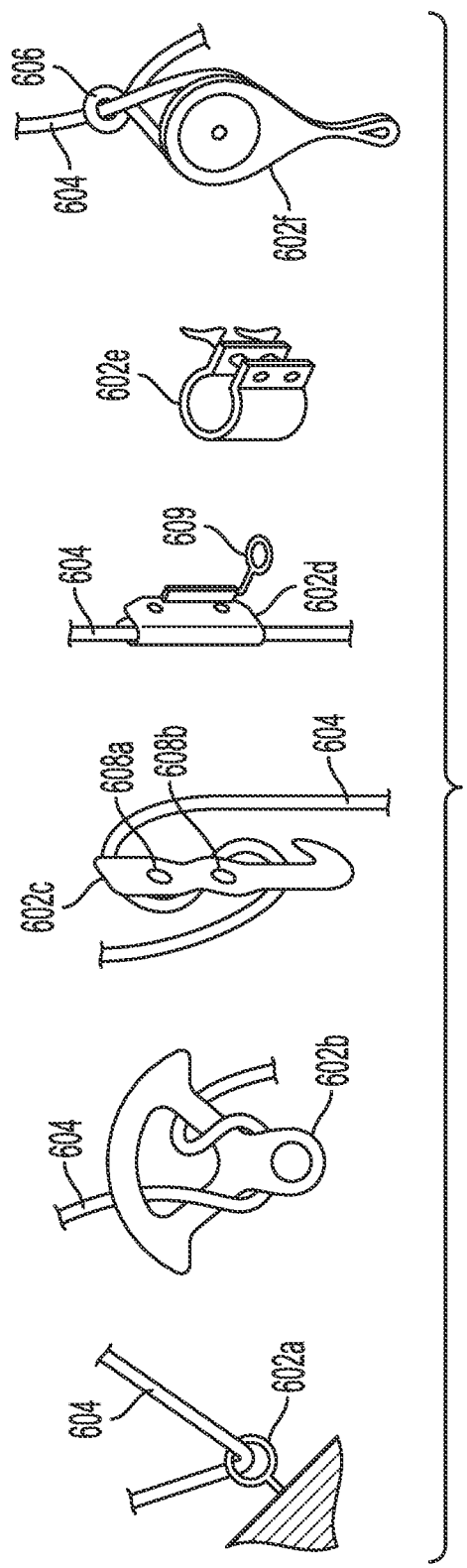
FIG. 6A through FIG. 6D illustrate various example descender units for releasably connecting a medical device to a descent line.

Turning to FIG. 6A, in some implementations, a descent line 604 is looped through a static descender unit 602. The static descender units 602 may be formed of a strong, rigid material such as stainless steel or another metal. Each of the descender units 602 illustrated, for example, may be connected to a surface of a medical equipment deployment unit. For example, the descender units 602 may be anchored to the medical equipment deployment unit using a screw or bolt. In another example, certain descender units may be built into the medical device, for example into a handle and/or a housing of the medical device such as medical device 1200 described in further detail below. A surface treatment on one or more surfaces of each descender unit 602 configured to contact the descent line 604 may increase frictional force between the descender unit 602 and the descent line 604. An eyelet type descender unit 602a includes a single opening for feeding the descent line 604 through the descender unit 602a. While simple, fairly small, and inexpensive to produce, the eyelet type descender unit 602a provides a least amount of friction of all of the illustrated descender units 602. A figure-eight type descender unit 602b is configured to receive the descent line 604 in an over/under looped configuration as illustrated. The looping configuration provides additional friction to the descent line, while the design remains relatively simple to produce and use. An S-feed descender unit 602c accepts the descent line 604 in a weaving s-path through a series of three openings. In some embodiments, the descent line 604 weaves around or between one or more rotating wheels or pins 608a, 608b providing frictional resistance to the descent line 604. In other embodiments, the S-feed descender unit 602c includes one or more textured pins 608a, 602b to increase frictional engagement with the descent line 604. The more complex path may increase frictional force against the travel of the descent line, while the more complex design of the S-feed descender unit 602c may increase cost of the unit. A clamp type descender unit 602d or 602e clamps against the descent line 604, surrounding the descent line 604 with frictional force. The clamp type descender units 602d and 602e have a smaller footprint than the majority of the descender units 602. The clamp type descender unit 602d includes a circular hook member 609 for attachment to a payload, such as the medical equipment deployment unit 102. The payload will apply a downward force, causing an internal brake mechanism to engage against the descent line 604. The clamp type descender unit 602e includes a set of butterfly bolts for manually setting a selected variable resistance. The variable resistance, for example, may be tuned for different deployment scenarios (e.g., drop height, payload weight, etc.). A snatch block type descender unit 602f provides a pulley effect by looping the descent line 604 around a wheel. A sliding knot 606 in the descent line 604 provides a belaying effect with tension in an upper direction of the descent line 604 (e.g., where the line is fed from the aerial delivery device) and gravitational force of a downward direction of the descent line 604.

Figure 6B:
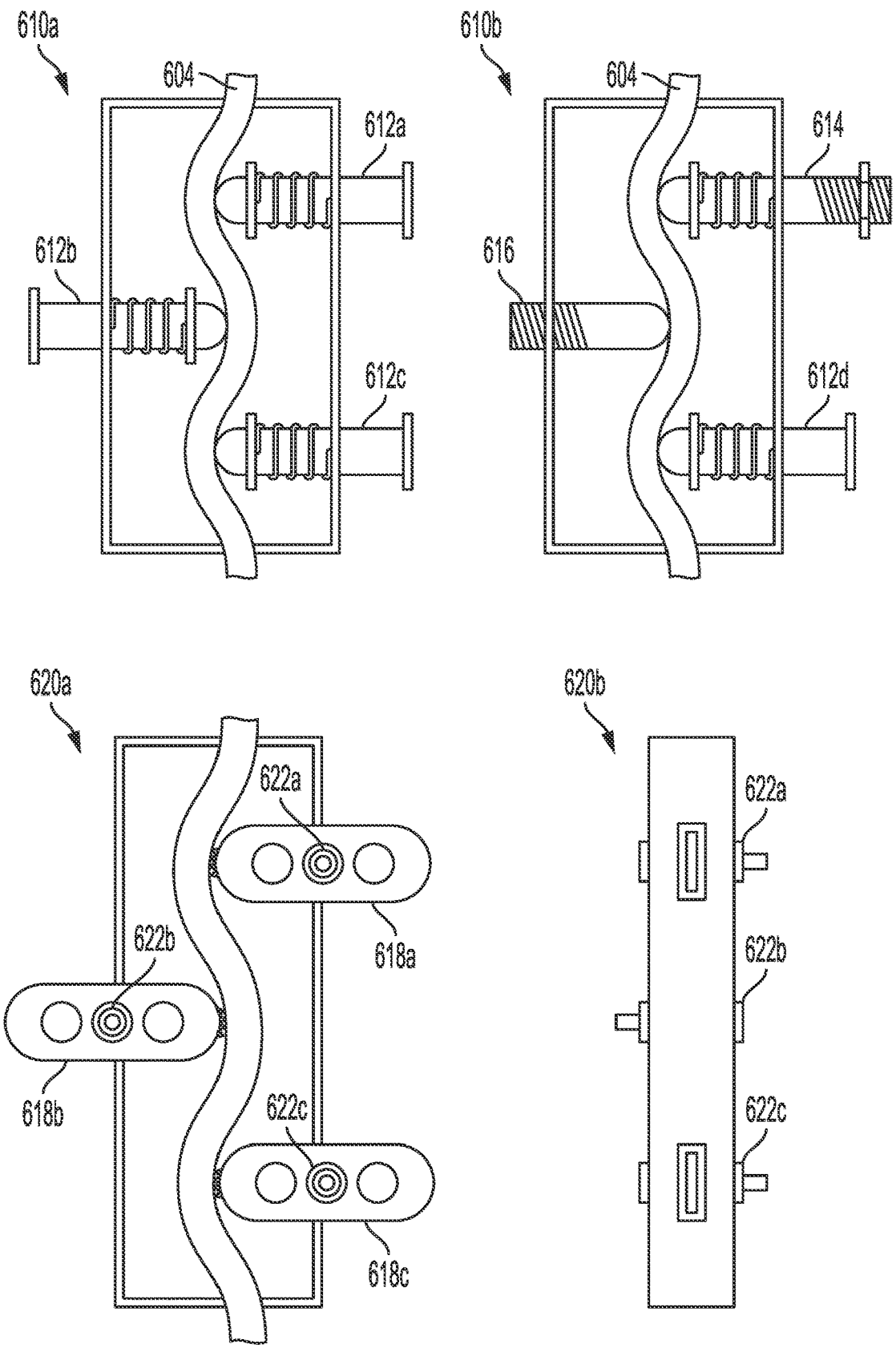

Turning to FIG. 6B, in some implementations, the descent line 604 is fed through a descender unit 610 or 620 including an offset configuration of friction pins arranged to force the descent line 604 into a curved path of motion between individual friction pins. The friction pins, in some embodiments, push the descent line 604 against an opposing wall of the descender unit 610, 620 housing, creating an additional frictional engagement. The inner housing of the descender unit 610, 620 may include a texturized or otherwise frictionally adjusted surface to increase this frictional engagement. The friction pins can include active and/or passive components. Although each example descender unit 610 or 620 includes three friction pins, in other configurations, more or fewer friction pins may be used. In further embodiments, entry and exit points may be offset and/or redirected (e.g., through a side wall of the descender unit 610 or 620 to adjust an amount of frictional load on the descender unit 610 or 620. Although illustrated in vertical alignment, implementations of the descender units 610 and 620 may be used in horizontal or vertical alignment.

In a first descender unit configuration 610a, spring-loaded friction pins 612a, 612b, and 612c are arranged to produce an "S" curve in the descent line 604 while applying spring tension force and frictional force to the descent line 604 during its travel through the descender unit configuration 610a. As the descent line 604 travels between the spring-loaded friction pins 612a-c, a spring element of each of the spring-loaded friction pins 612a-c exerts a horizontal force that fights against the downward force on the descent line 604 which would otherwise cause the descent line 604 to travel in a straight line. The tips of each of the friction pins 612a-c, further, applies a frictional force relative to the downward force of the descent line 604. This frictional force may be enhanced by a surface area and/or texture of the tips of the friction pins 612a-c.

In a second descender unit configuration 610b, a spring-loaded, variable length friction pin 612, a rigid friction pin 616 with variable length, and a spring-loaded friction pin 612d are arranged to produce an "S" curve in the descent line 604 while applying variations of spring tension force and frictional force to the descent line 604 during its travel through the descender unit configuration 610b. The length of the spring loaded, variable length friction pin 614 and/or the variable length rigid friction pin 616 may be adjusted, for example, using a bolt thread and nut configuration. In another example, the length of the friction pin 614 and/or the friction pin 616 may be adjusted through threaded engagement with a housing of the descender unit.

In a third descender unit configuration 620, planar friction pins 622 with selectable length settings are arranged to produce an "S" curve in the descent line 604 while applying frictional force to the descent line 604 during its travel through the descender unit configuration 620. A descent line-engaging face of each of the planar friction pins 622 may be enhanced with a texture to increase frictional engagement with the descent line 604. As illustrated, each of the planar friction pins 622 is mounted to the descender unit configuration 620 through a center opening of three selectable openings using a corresponding bolt and nut 622a, 622b, and 622c. In other implementations, more or fewer selectable openings may be provided. Additionally, in further implementations, the selection of length setting for each friction pin 622 may be different.

The friction pins 612, 614, 616, and/or 618 of the configurations 610a, 610b, and 620, in some embodiments, are each fixed to an exterior shell of the corresponding descender unit, not illustrated. The descender unit, in this example, may be attached to a surface of a medical equipment deployment unit. In other embodiments, the friction pins 612, 614, 616, and/or 618 of the configurations 610a, 610b, and 620 are each fixed to a frame or cage designed to surround at least a portion of a medical device. In this example, the descent line 604 is fed through the built-in descender unit of the medical equipment deployment unit.

Figure 6C:
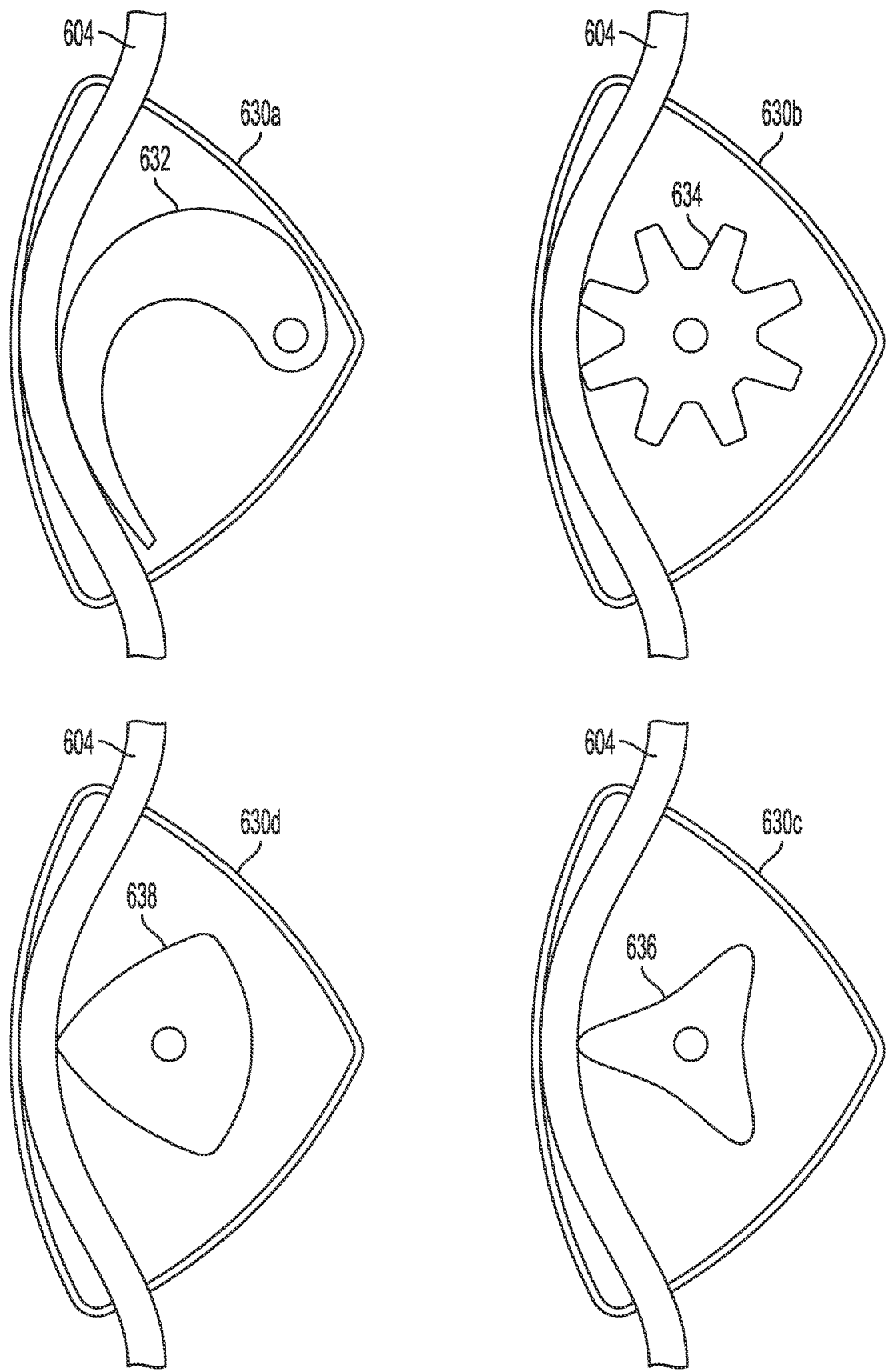

Turning to FIG. 6C, in some implementations, the descent line 604 is fed through a descender unit 630a-d including a rotatable feature 632, 634, 636, or 638 to apply a rotational counter force to the motion of the descent line 604 through the descender unit 630a-d. The rotational feature (e.g., cam), as illustrated, may be formed in a variety of shapes, such as a hook cam 632, a starburst cam 634, a three-point cam 636, or a curved triangle cam 638. The rotational features 632, 634, 636, and 638, in some examples, may each supply a spring-driven counter-force or a gravity-driven counter-force to the descent line 604. Further, the rotational features 634, 636, and 638 may pinch the descent line 604 against an inner surface of the descender unit 630b-d, as illustrated with rotational feature 638 of a descender unit 630d. The descender units 630a-d may be horizontally mounted (e.g., on a top of the medical device unit in orientation for descent) or vertically mounted (e.g., on a side of the medical device unit in the orientation for descent). If vertically mounted, in some embodiments, two descender units 630 may be mounted on parallel sides of the medical device unit, similar to the two-descent line configuration illustrated in FIG. 5.

Figure 6D:
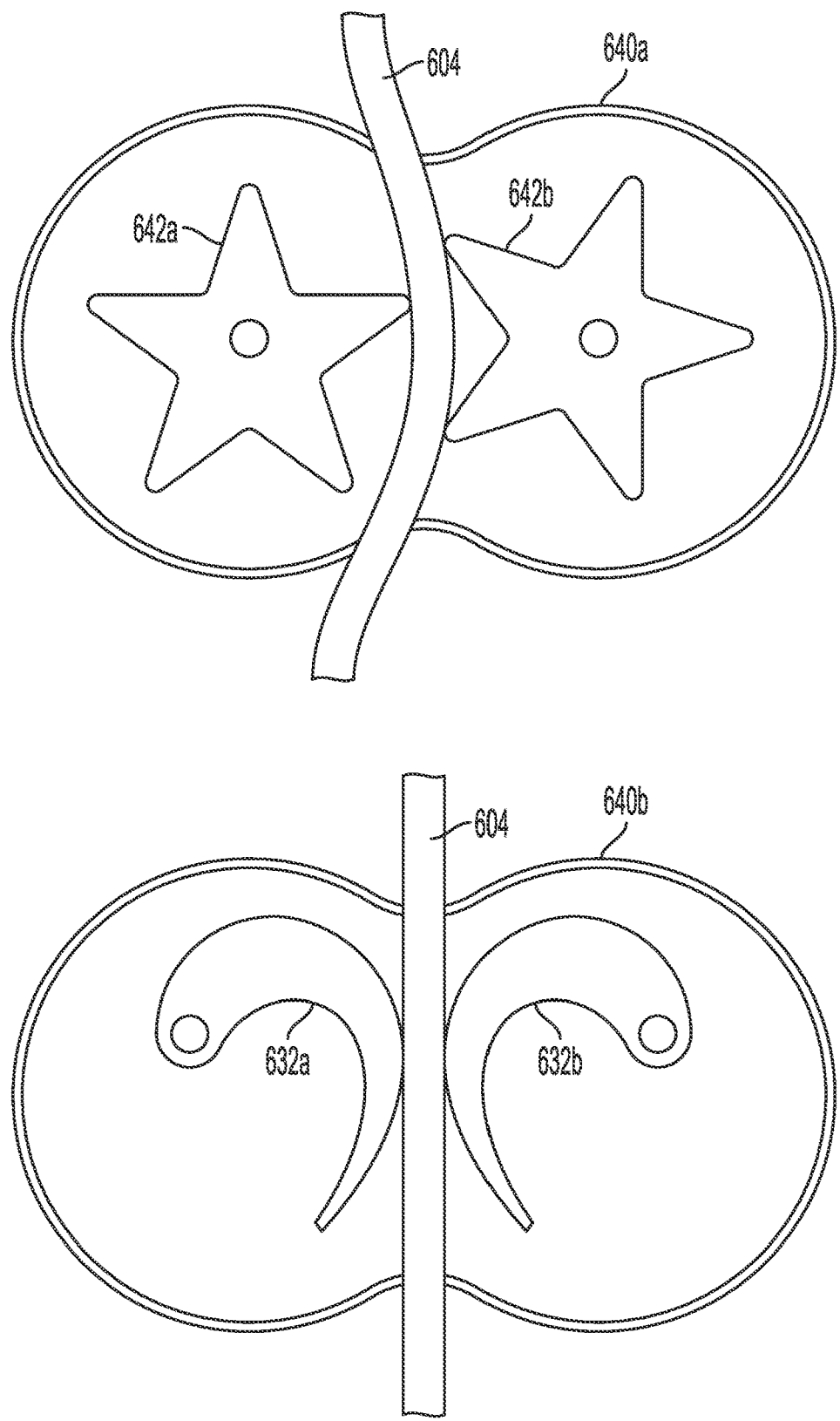

As shown in FIG. 6D, in some implementations, the descent line 604 is fed through a descender unit 640a,b including a pair of rotatable features 642 or 632 to apply rotational counter forces to the motion of the descent line 604 through the descender unit 640a,b. As with FIG. 6C, the rotational feature (e.g., cam), as illustrated, may be formed in a variety of shapes, such as a pair of star cams 642a, 642b or a pair of hook cams 632a, 632b. The rotational features 632 and 642, in some examples, may each supply a spring-driven counter-force or a gravity-driven counter-force to the descent line 604. While more complex than the single cam descender units 630 of FIG. 6C and likely a bit heavier and more expensive, in some embodiments, the dual cam descender units 640 may be preferred because the forces on the descent line 604 in the non-vertical direction are balanced by the two opposing cams, thus avoiding a tilt or swinging of the medical device unit during the drop.

Figure 7A:
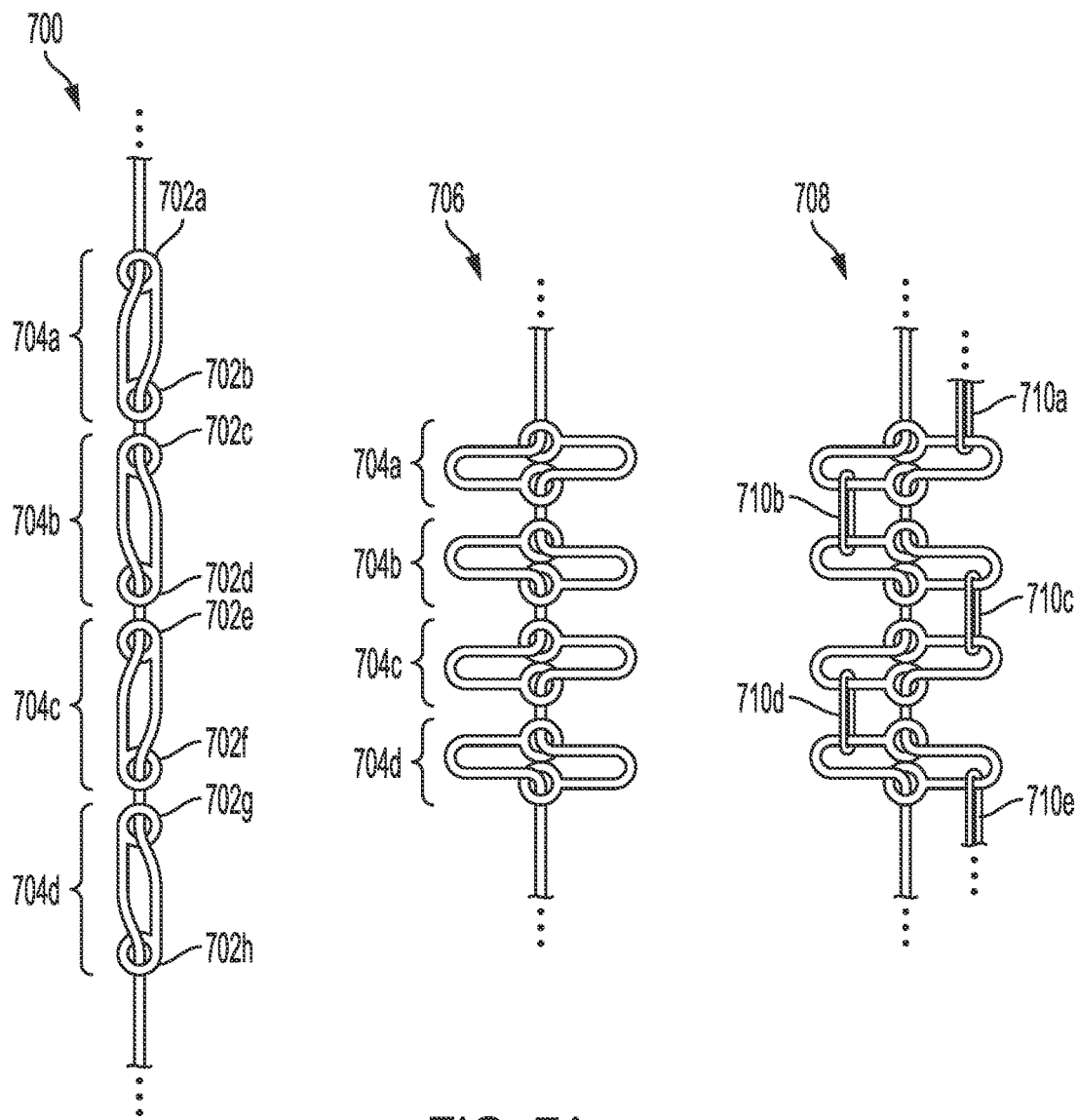
FIG. 7A illustrates a first example descent slowing apparatus including a slow extension descent line for limiting acceleration of a medical device dropped to the location of an emergency medical event.
Figure 7B:
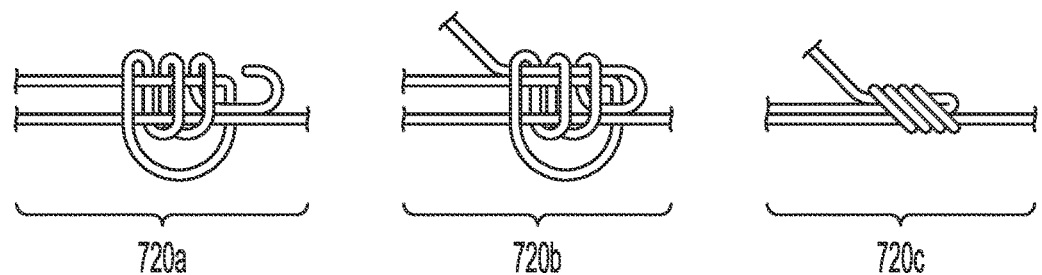
FIG. 7B illustrates an example knot configuration for use with the example descent slowing apparatus of FIG. 7A.
Figure 7C:
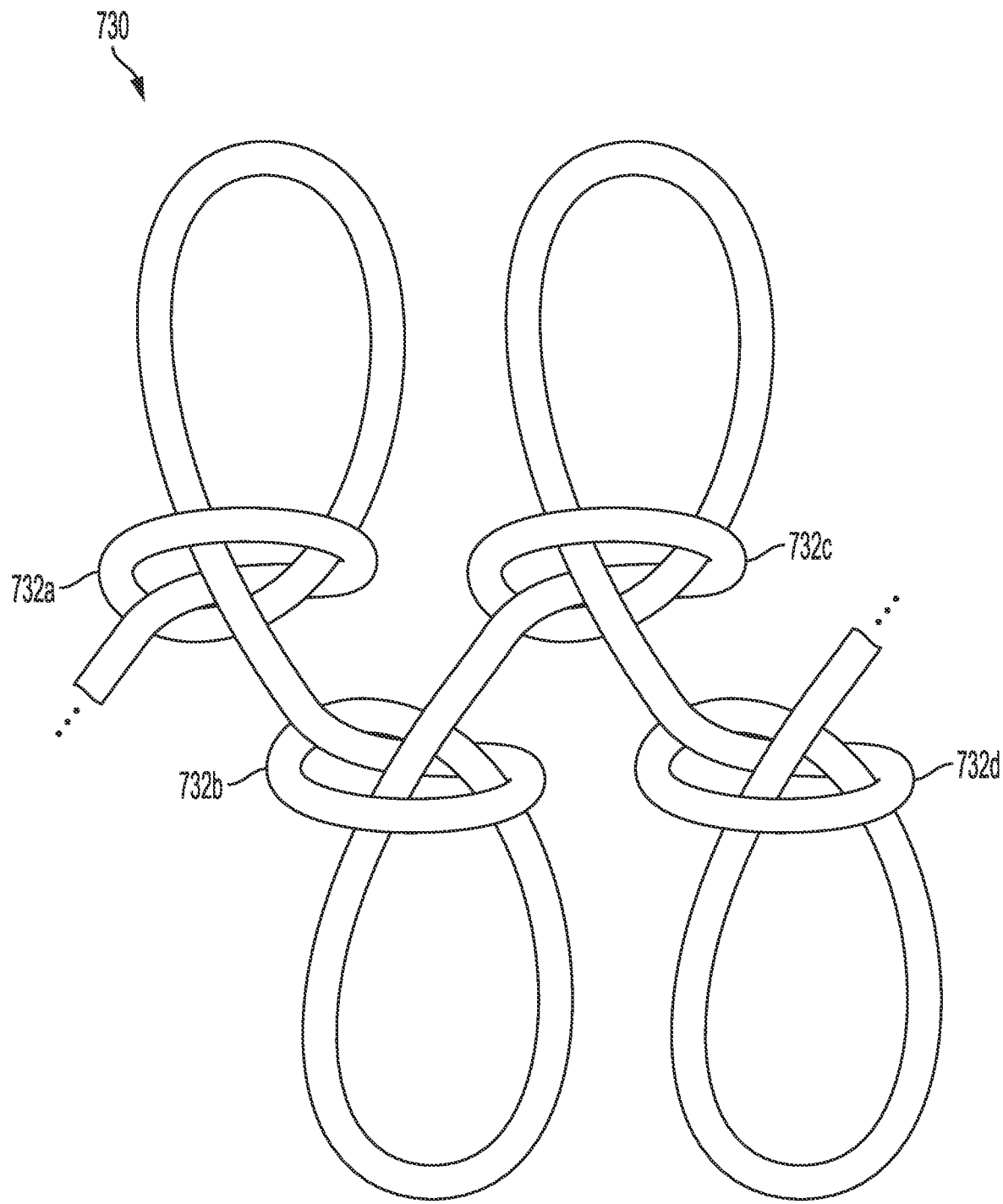
FIG. 7C illustrates a second example knot configuration for limiting acceleration of a medical device dropped to the location of an emergency medical event.
Figure 8:
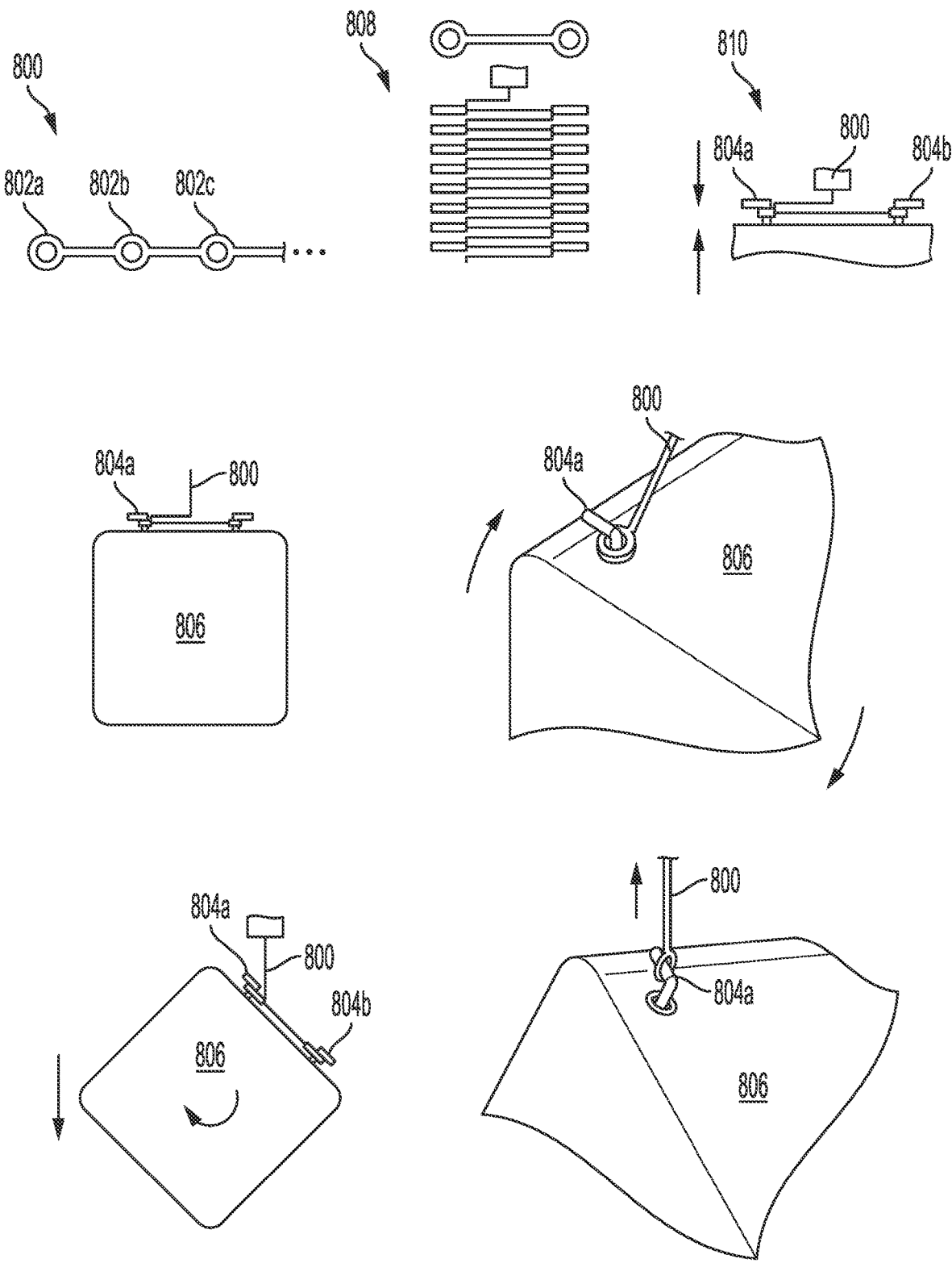
FIG. 8 illustrates a second example descent slowing apparatus including a slow extension descent line for limiting acceleration of a medical device dropped to the location of an emergency medical event.

FIG. 7A, FIG. 7C, and FIG. 8 illustrate example descent slowing apparatus including slow extension descent line configurations for limiting acceleration of a medical device dropped to the location of an emergency medical event. The descent lines, in some examples, may be formed of lightweight flexible cord, rope, twine, or line such as fishing line. The descent lines may be textured, in some embodiments, to increase friction.

As illustrated in FIG. 7A, for example, a first slow extension descent line configuration 700 includes a series of sliding knots 702, such as a slip knot, figure eight knot, or barrel knot, configured to create a series of doubled descent line segments 704. FIG. 7B illustrates a series of steps 720a, 720b, and 720c for tying an example knot 702. One end of the descent line configuration 700 may be connected to the aerial delivery vehicle, for example, and the other end of the descent line configuration 700 may be connected to the medical equipment deployment unit. When the medical equipment deployment unit is dropped from the aerial delivery vehicle, the weight of the medical equipment deployment unit on the descent line configuration 700 pulls on the knots, causing the knots to slowly slide, segment by segment, extending the double descent line segments 704 into a unitary line. For example, knot 702 may slide to contact knot 702a, and knot 702c may slide to contact knot 702d. The type of descent line 700, the type of the knots 702, the tightness of the knots 702, and/or the length of each segment 704 may be adjusted to control descent acceleration. Thus, depending upon the weight of the medical equipment deployment unit, the height of the drop, and/or a maximum acceleration rating for the medical equipment deployment unit, components of the descent line configuration 700 may be adjusted to ensure safe delivery of the medical equipment deployment unit to the location of the emergency medical event.

The descent line configuration 700, in some embodiments, is designed to extend an entire length of the anticipated drop. In other embodiments, the descent line configuration 700 is designed to extend a portion of the length of the anticipated drop, such that a portion of untethered fall is limited. For example, a breakaway element may be designed into the descent line configuration 700, a connector at the aerial delivery vehicle end, and/or a connector at the medical equipment deployment unit end to release the medical equipment deployment unit without manual intervention (e.g., untying or unclipping the descent line configuration 700 from the medical equipment deployment unit prior to use).

To further control extension of the descent line, in some implementations, as shown in a descent line configuration 706, the doubled descent line segments 704 may be separated and pulled outwards, causing the knots 702 to stack against one another. In the descent line configuration 706, when the medical equipment deployment unit is dropped from the aerial delivery vehicle, the weight of the medical equipment deployment unit on the descent line configuration 706 pulls to separate the knots 702 (e.g., into the first descent line configuration 700) and then further pulls to extend the double descent line segments 704 into a unitary line.

In additional implementations, as shown in a descent line configuration 708, after pulling apart the doubled descent line segments 704 as illustrated in the descent line configuration 706, the separated portions may be tied, clipped, or adhered together as illustrated by a series of releasable connections 710. In the descent line configuration 708, when the medical equipment deployment unit is dropped from the aerial delivery vehicle, the weight of the device on the rope pulls to separate the knots 702 (e.g., into the first descent line configuration 700), causing the releasable connections 710 to release or break. The weight of the medical equipment deployment unit on the descent line 708 then further pulls to extend the double descent line segments 704 into a unitary line.

FIG. 7C illustrates a second example knotted descent line configuration 730 for limiting acceleration of a medical device dropped to the location of an emergency medical event. As illustrated, the descent line configuration 730 includes a series of slip knots 732. One end of the descent line configuration 730 may be connected to the aerial delivery vehicle, for example, and the other end of the descent line configuration 730 may be connected to the medical equipment deployment unit. When the medical equipment deployment unit is dropped from the aerial delivery vehicle, the weight of the medical equipment deployment unit on the descent line configuration 730 pulls on the knots 732, causing the knots 732 to individually pull loose and extending the descent line configuration 730 into a unitary line.

Turning to FIG. 8, an example descent line configuration 800 includes a series of loops 802 spaced at regular intervals along the descent line. The loops 802 may be formed into the material of the descent line, such as holes cut into the material or eyelets pierced through the material. The loops 802, in a further example, may be tied as loop knots into the descent line.

In some implementations, the loops 802 are configured to slip over a set of hooks 804a, 804b connected to a medical equipment deployment unit 806. As shown in a descent line configuration 808, for example, the descent line may be folded back and forth along the intervals between the loops 802 to stack sets of the loops 802. The stack, for example, may be created by attaching loops back and forth between the set of hooks 804a, 804b as illustrated in a descent line attachment configuration 810.

In use, the medical equipment deployment unit 806 is dropped, in some implementations, from an aerial delivery vehicle. The loops 802 of descent line configuration 808 begin to release, one after another, from the set of hooks 804a, 804b, where releasing entails releasing from one hook 804a, 804b to the other hook 804b, 804a, repeatedly. During the descent, as the loops 802 release from the set of hooks 804a, 804b, the medical equipment deployment unit 806 will gently and controllably swing due to tension switching from the first hook 804a, 804b to the second hook 804b, 804a and back, where each gentle swing assists in releasing the next loop 802 from its associated hook 802a, 802b. Upon a final loop disconnecting from the medical equipment deployment unit 806, if the medical equipment deployment unit 806 has not yet contacted the ground, the medical equipment deployment unit 806 may fall for the remainder of the distance between the aerial delivery unit and the location of the emergency medical event.

Figure 9A:
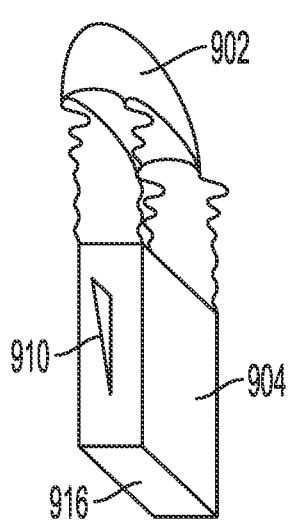
FIG. 9A through FIG. 9C illustrate example descent slowing apparatus for limiting free fall acceleration of a medical device dropped to the location of an emergency medical event.
Figure 9B:
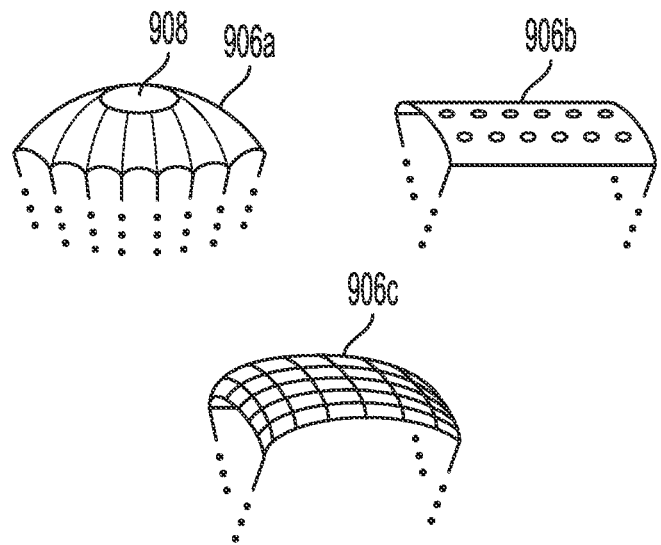
Figure 9C:
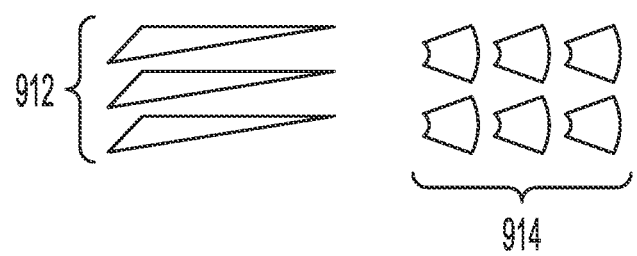

FIG. 9A through FIG. 9C illustrate example descent slowing apparatus for limiting free fall acceleration of a medical device dropped to the location of an emergency medical event. The descent slowing apparatus, for example, may be connected to a medical device or to a frame, cage, or harness coupled to the medical device (the combination thereof a medical equipment deployment unit) to limit acceleration of the medical device when dropped from an aerial delivery vehicle. The descent slowing apparatus is configured, in some embodiments, to avoid inhibiting use of the medical device once it has reached the ground at the location of the emergency medical event. For example, the descent slowing apparatus may be positioned on surfaces of the medical device away from controls and tools needed by a rescuer to perform an emergency medical procedure. In other embodiments, the descent slowing apparatus is configured for quick release from the medical device prior to use of the medical device. For example, the descent slowing apparatus may be coupled to a quick release frame, cage, or harness at least partially surrounding the medical device.

As shown in FIG. 9A, in some embodiments, a parachute 902 is coupled to one or more surfaces of a medical device to provide resistance against free fall acceleration toward the ground. The parachute 902, for example, may be folded or packed against the medical equipment deployment unit 904 in transit to the location of the emergency medical event and may automatically upon when the medical equipment deployment unit 904 is dropped from the aerial delivery vehicle. The parachute 902 may be designed of lightweight material(s) such as, in some examples, natural fabric, plastic canvas, and/or nylon. In some embodiments, the parachute 902 includes water resistant or waterproof materials in the event of rain or snow during deployment.

FIG. 9B illustrates example parachutes 906 for coupling to the medical device 904. While the parachute 902 is illustrated as having a solid material design, in some embodiments, to avoid the effect of wind on the trajectory of the medical equipment deployment unit 904, a parachute 906 with air openings may be used to provide acceleration resistance while maintaining a generally downward direction of the medical equipment deployment unit 904. Parachute 906*a* includes a central opening 908 for controlled air diversion through the parachute 906*a*. Parachute 906*b* includes spaced openings or perforations for controlled air diversion through the parachute 906*b*. Parachute 906*c* is formed of a mesh or net material for controlled air diversion through the parachute 906*b*. Other designs are possible, such as modifications or combinations of the illustrated designs (e.g., the central opening 908 of the parachute 906*a* in addition to smaller perforations as those illustrated on parachute 906*b*).

Returning to FIG. 9A, in some implementations, air flow diverters, such as an air flow diverter 910, are coupled to the medical equipment deployment unit 904 to provide acceleration resistance while maintaining a generally downward direction of the medical equipment deployment unit 904. In some embodiments, the air flow diverters are designed from lightweight rigid material, such as plastic. Rigid material, for example, may maintain position and shape to accurately deflect air in a desired direction. In other embodiments, the air flow diverters are designed from semi-rigid or flexible material. In some examples, the material may include silicone, rubber, and/or foam (e.g., ethylene-vinyl acetate (EVA) or polyurethane). Semi-rigid or flexible material, for example, may be compressed or partially compressed in transit. Further, a semi-rigid or flexible material may avoid cracking or breaking of the air flow diverter upon impact, increasing the ability to reuse the frame, cage, or harness surrounding the medical device.

Turning to FIG. 9C, the flow diverters may include at least two fin diverters 912 such as the fin-style air diverter 910 illustrated as attached to one vertical side of the medical equipment deployment unit 904 (e.g., in a direction of drop in relation to the parachute 902). An opposite vertical surface of the medical equipment deployment unit 904 may include a second, matching fin diverter 912. The fin diverters 912, in some embodiments, may be used in embodiments without parachutes to maintain a direction of fall of the medical equipment deployment unit. For example, the fin diverters 912 may be positioned to encourage falling upon a most robust surface of the medical equipment deployment unit 904 to avoid additional damage.

In some implementations, air flow diverters are designed to provide both directional flow control and deceleration assistance. As shown in FIG. 9C, for example, a set of open cone diverters may be aligned along two or more surfaces of the medical equipment deployment unit 904 such air is directed upward into a wide portion of the open cone and directed through a small portion of the open cone. Further, in some embodiments, a series of two or more cones may be positioned in vertical alignment to repeatedly control air flow along the medical equipment deployment unit 904, thus increasing the ability of the diverters 914 to decelerate the drop of the medical equipment deployment unit 904 toward the ground.

In some implementations, to control the drop of the medical equipment deployment unit, impact absorbing apparatus is coupled to the medical device and/or to a frame, harness, or cage partially surrounding the medical device to absorb the fall impact to the medical equipment deployment unit when dropped to the location of the emergency medical event. The impact absorbing apparatus may be weighted, at least in part, to encourage landing upon a select surface of the medical equipment deployment unit. For example, a weighted impact absorbing feature may be coupled to a surface of the medical device that is least prone to damage upon impact. In this manner, impact absorbing apparatus may be selectively attached to the medical device while reducing an overall footprint of the medical equipment deployment unit being deployed by the aerial delivery vehicle.

Figure 10A:
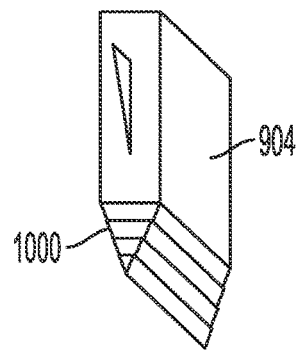
FIG. 10A through FIG. 10D illustrate example impact absorbing apparatus for absorbing fall impact to a medical device dropped to a location of an emergency medical event.
Figure 10B:
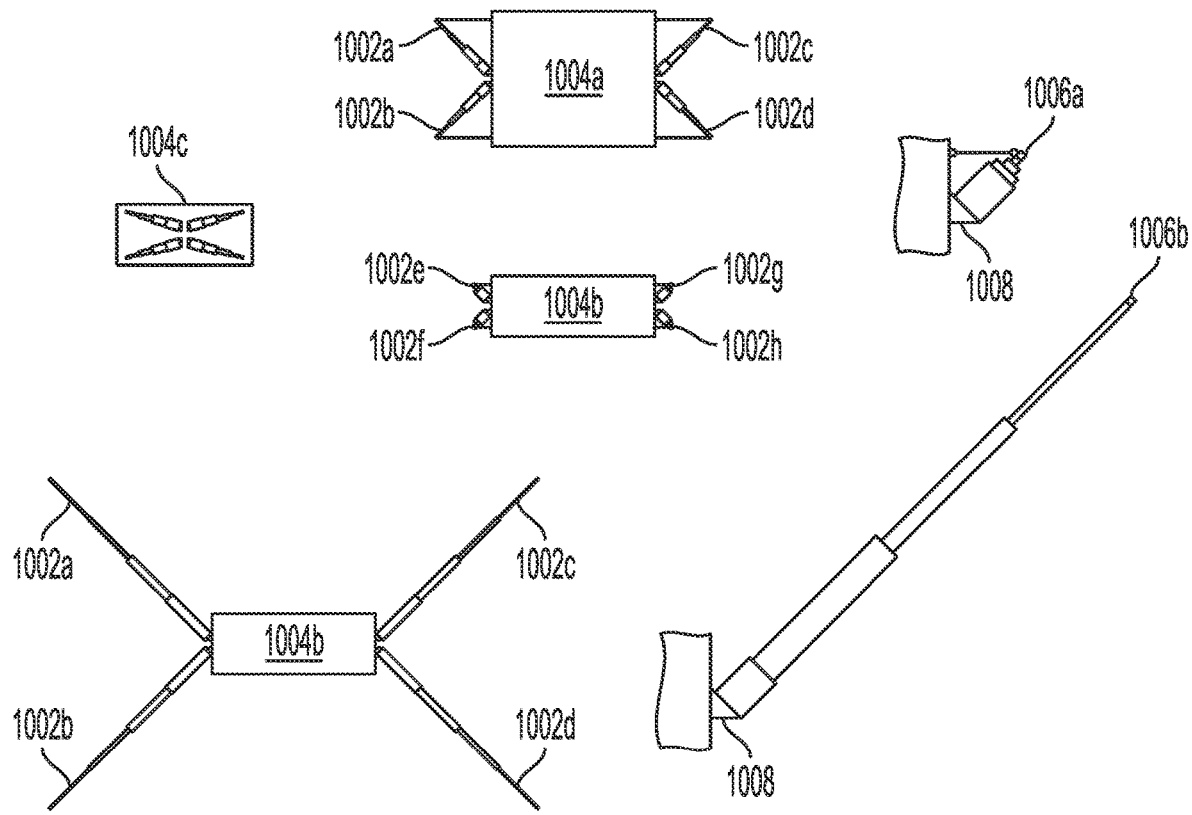
Figure 10C:
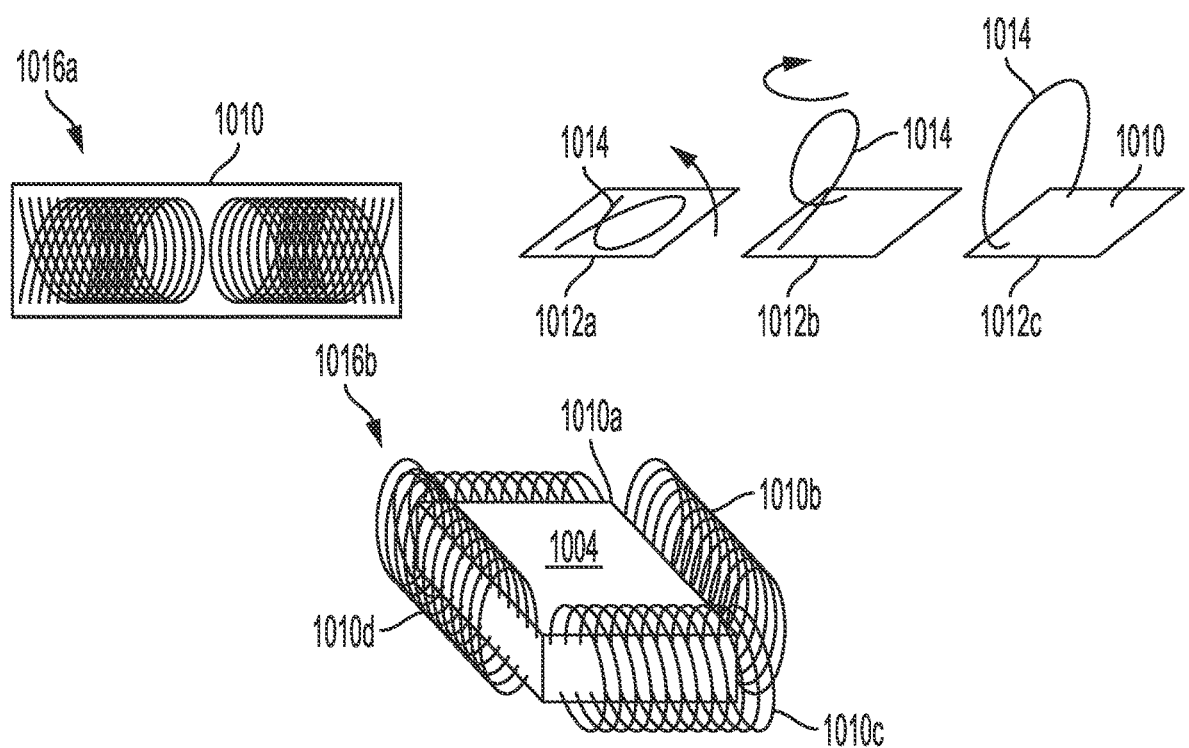
Figure 10D:
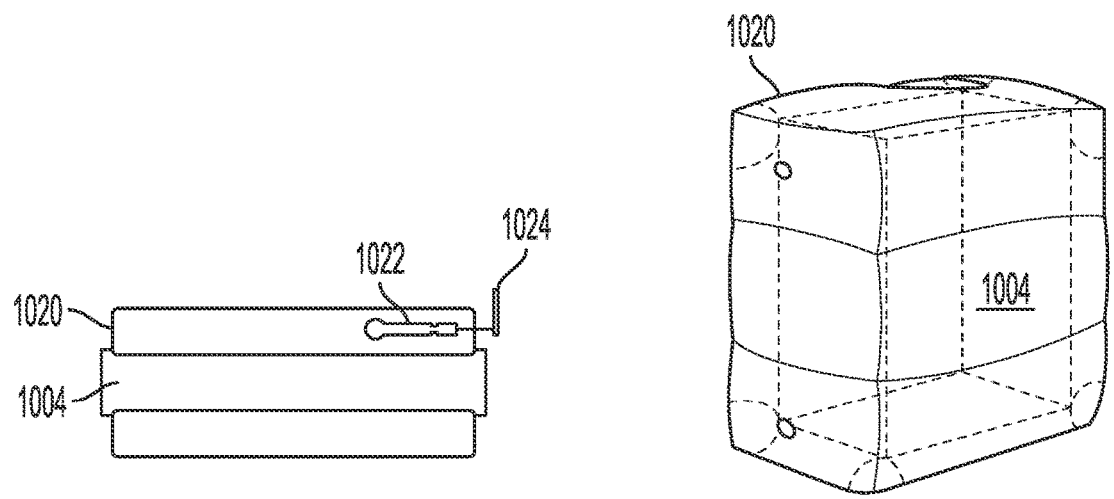

FIG. 10A, FIG. 10C, and FIG. 10D illustrate examples of impact dampening elements for absorbing the force of impact of medical equipment dropped to the site of a medical event. Various impact dampening elements may be releasably attached to medical equipment or to an apparatus enclosing the medical equipment, such as a frame, cage, harness, or case. In further examples, the apparatus enclosing the medical equipment may include a stretchable or flexible sleeve or envelope that wraps the medical equipment and provides a base for connection of impact dampening elements. In some examples, the impact dampening elements may be attached using a quick release connector such as hook and loop material, a locking rail and slide, a buckle, or a rotating lock connector.

Turning to FIG. 10A, a shock absorber 1000, such as a hollow corrugated bumper, may be attached to a surface 916 of the medical equipment deployment unit 904 opposite the parachute 902, as illustrated in FIG. 9A. The shock absorber 1000, in some implementations, is produced from disposable materials, such as cardboard. The disposable shock absorber, for example, may be designed to controllably break, thus dampening the impact of the medical equipment deployment unit 904 when impacting the ground at the location of the emergency medical event. In other implementations, the shock absorber 1000 is produced from reusable materials, such as silicone, EVA, or polyurethane. A reusable shock absorber, for example, may be coupled to the medical device itself or to a reusable frame, harness, or cage. Further, in the event that the reusable shock absorber may be compressed during transit, an overall footprint of the medical equipment deployment unit may be reduced.

In some implementations, turning to FIG. 10B, a set of expandable shock absorbing arms 1002 are connected to a medical equipment deployment unit 1004 for dampening the impact of the medical equipment deployment unit 1004 when it reaches the ground at the location of the emergency medical event. For example, as illustrated in a front view 1004a, a rear view 1004b, and a side view 1004c, an "x" pattern of four expandable arms 1002 may be arranged on opposing sides of the medical equipment deployment unit 1004 in a retracted configuration. While retracted, for example, the expandable arms 1002 may be arranged within a border of each of the sides of the medical equipment deployment unit 1004 (e.g., as illustrated in the side view 1004c).

As illustrated in a retracted configuration 1006a, in some implementations, each expandable arm 1002 may be mounted to the medical equipment deployment unit 1004 at an angle to a surface of the medical equipment deployment unit 1004. A connector 1008 may rigidly or flexibly engage each expandable arm 1002 with the medical equipment deployment unit 1004. For example, a spring-loaded or rubberized dampening connector may provide additional impact dampening and avoid damage to the expandable arm 1002 from impact forces in directions other than the extension direction of the expandable arms 1002.

Turning to an extended configuration 1006b, in some implementations, a spring-loaded or pneumatic release may cause telescoping extensions to expand out from the retracted configuration 1006a. The mechanical or pneumatic spring force, for example, may cushion impact by absorbing forces of impact received in a direction of extension of the expandable arm 1002.

In use, in some implementations, the expandable arms 1002 may be compressed into the retracted configuration 1006a against surfaces of a payload region of the aerial delivery vehicle. When dropped above the location of the emergency medical event, the expandable arms 1002 may automatically extend. In other implementations, a manual release trigger, such as a clip or tie to the aerial delivery vehicle that unties or breaks as the medical equipment deployment unit 1004 descends, may be used to trigger extension of the expandable arms 1002. The manual trigger, for example, may be designed to trigger extension of the expandable arms 1002 at approximately a selected distance beneath the aerial delivery vehicle. In further implementations, an electronic release trigger, such as a gyroscope or accelerometer, may be used to automatically trigger extension of the expandable arms 1002 when a certain acceleration or velocity is achieved.

Turning to FIG. 10C, in some implementations, one or more expandable spring cage panels 1010 are aligned along surfaces of the medical equipment deployment unit 1004 to absorb impact forces when the medical equipment deployment unit 1004 drops to the ground at the location of an emergency medical event. Each spring cage panel 1010 includes a set of springs, such as illustrative spring 1014, that lie against the spring cage panel 1010 in a retracted state 1016a and extend upward, downward, and outward from the surface of the spring cage panel 1010 in an expanded state 1016b. The set of springs, in some implementations, are individual loops aligned in series along the panel 1010. In other implementations, the set of spring loops are loops of a single spring element. The spring loops may be made from a flexible metal wire or polymer spring material. Polymer spring material may be lighter weight, for example, while metal wire springs may be less expensive.

As illustrated in the expanded state 1016b, four spring cage panels 1010a, 1010b, 1010c, and 110d are arranged along the four sides of the medical equipment deployment unit 1004. The spring cage panels 1010a-d, in some embodiments, form at least a portion of a protection frame or cage surrounding a medical device. In use, for example, the medical device may be releasably secured in the protection frame including the spring cage panels 1010a-d and positioned in a cargo region of an aerial delivery vehicle in the compressed state 1016a. Upon release from the aerial delivery vehicle, the springs of the spring cage panels 1010a-d may expand into the expanded state 1016b, thereby protecting the medical device from damage while being dropped to the location of a medical emergency event.

A series of illustrations 1012 present an example configuration for compression and release of the springs on a spring cage panel. As shown in the illustrations 1012, in a compressed configuration 1012a, the spring 1014 is twisted and lying substantially flat against the panel 1010. While expanding 1012b, the spring 1014 pops up to be substantially perpendicular to the panel 1010. In an expanded configuration 1012c, the spring 1014 is untwisted and substantially perpendicular to the panel 1010.

Turning to FIG. 10D, in some implementations, one or more airbags or air bladders 1020 are arranged to at least partially surround a medical device and inflate when the medical equipment deployment unit 1004 is released from an aerial delivery vehicle to protect the medical device from impact forces upon landing at the location of an emergency medical event. The air bags or bladders 1020, for example, may be designed in a toroidal shape to surround four sides of the medical equipment deployment unit 1004. In another example, the air bags or bladders 1020 may encompass the medical equipment deployment unit 1004. For example, the medical equipment deployment unit 1004 may be inserted into an air bag envelope which, when inflated, surrounds the six surfaces of the medical equipment deployment unit 1004 with one or more air bladders.

The air bag or air bladders 1020, in some implementations, automatically fill with surrounding air when the medical equipment deployment unit 1004 is dropped from the aerial delivery vehicle. For example, the air bag or air bladders 1020 may include rigid or semi-rigid intake vents for receiving air. Air flow diverters, such as the diverters 912 and/or 914 of FIG. 9C may be arranged to maintain an orientation of the medical equipment deployment unit 1004 allowing for filling of the air bag or bladders 1020. Further, air flow diverters may be arranged to direct air into the air bag or bladders 1020 to encourage rapid filling of the air bag or bladders. The air bag or bladders, in this circumstance, may initially behave as a parachute, slowing the acceleration of the medical equipment deployment unit 1004 while filling to protect the medical equipment deployment unit 1004 from impact damage once it reaches the ground.

In some implementations, the air bag 1020 includes an air cannister 1022 for automatically inflating the air bag 1020. The air cannister 1022 may contain a compressed gas such as carbon dioxide. The contents of the air cannister may be activated by igniting a propellant. The air cannister 1020 may be connected to a trigger mechanism 1024 configured to trigger release of compressed air to inflate the air bag 1020. The trigger mechanism 1024, in some embodiments, is a break-away connection to a surface of the payload region of the aerial delivery vehicle, designed to exert sufficient force to trigger release of air by the air cannister 1022 before breaking from connection to the aerial delivery vehicle. The break-away connection, in some examples, may be a loop of string or a rubber band connecting the medical equipment deployment unit 1004 to the payload region of the aerial delivery vehicle. In other embodiments, the trigger mechanism 1024 is a sensor such as a gyroscope or accelerometer, configured to trigger release of compressed air at a threshold velocity or acceleration. For example, a threshold g-force may be applied as a trigger event.

In some implementations, the air bag or bladders 1020 are reusable. For example, the air bag or bladders 1020 may be deflated and readied for additional use. In other implementations, the air bag or bladders 1020 are disposable. Inexpensive materials may be used, for example, for single use purpose. In this manner, retrieval of the air bag or bladders 1020 from the location of the emergency medical event is not needed, and there is no concern of loss of durability due to damage or stress applied to the air bag or bladders 1020 during a prior use.

Figure 11:
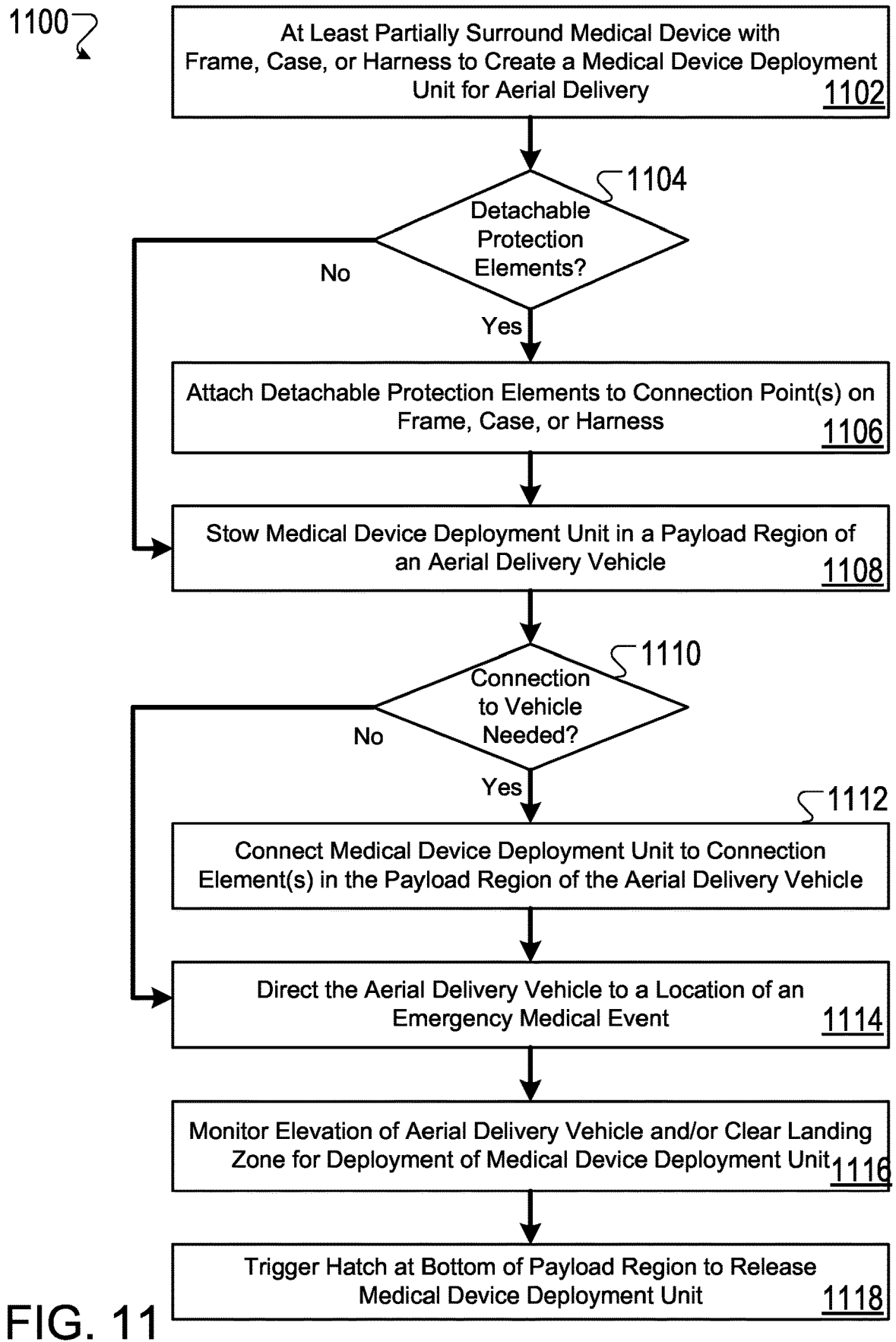
FIG. 11 is a flow chart of an example method for preparing and aerially deploying a medical device to an emergency medical event.

FIG. 11 is a flow chart of an example method 1100 for preparing and aerially deploying a medical device to an emergency medical event. The method 1100, for example, may be used to deliver a medical device, such as an Automated External Defibrillator (AED), to a location of an emergency medical event for use by a rescuer.

In some implementations, the method 1100 begins with at least partially surrounding a medical device with a frame, case, or harness to create a medical equipment deployment unit for aerial delivery (1102). The medical equipment deployment unit, for example, includes the medical device as well as one or more protection elements (e.g., deceleration elements and/or impact dampening elements), such as the various deceleration elements and impact dampening elements described above, to protect the medical device while dropping to a location of a medical emergency event. The frame, case, or harness may be designed to quickly release from the medical device once deployed to allow for rapid use of the medical device by a rescuer in providing therapy to an individual with a threatening medical condition.

In some implementations, if the medical device unit is designed to accept one or more detachable protection elements (1104), in some implementations, the detachable protection element(s) are attached to connection point(s) on the frame, case, or harness (1106).

In some implementations, the medical equipment deployment unit is stowed in a payload region of an aerial delivery vehicle (1108). For example, the medical equipment deployment unit 102 is stowed in the payload region 108 of the aerial delivery vehicle 106 as described above.

In some implementations, if a connection between the medical equipment deployment unit and the aerial delivery vehicle is needed (1110), the medical equipment deployment unit is connected to connection element(s) provided in the payload region of the aerial delivery vehicle (1112). The connection elements, for example, may include the reel 106 and/or the retractor 112 of FIG. 1A, the descender 218 of FIG. 2A, the braking reel 410 and/or the reel 412 of FIG. 4A, and/or the connection points for the first descender line 504a and the second descender line 504b of FIG. 5A.

In some implementations, the aerial delivery vehicle is directed to a location of an emergency medical event (1114). The aerial delivery vehicle may be remotely operated by a controller, for example, as described above.

In some implementations, elevation of the aerial delivery vehicle and/or a clear landing zone is monitored for deployment of the medical equipment deployment unit (1116). A controller remotely operating the aerial delivery vehicle, for example, may perform the monitoring, as described above.

In some implementations, a hatch at the bottom of the payload region is triggered to release the medical equipment deployment unit (1118). The hatch, for example, may be the hatch 114 as described above.

Figure 12:
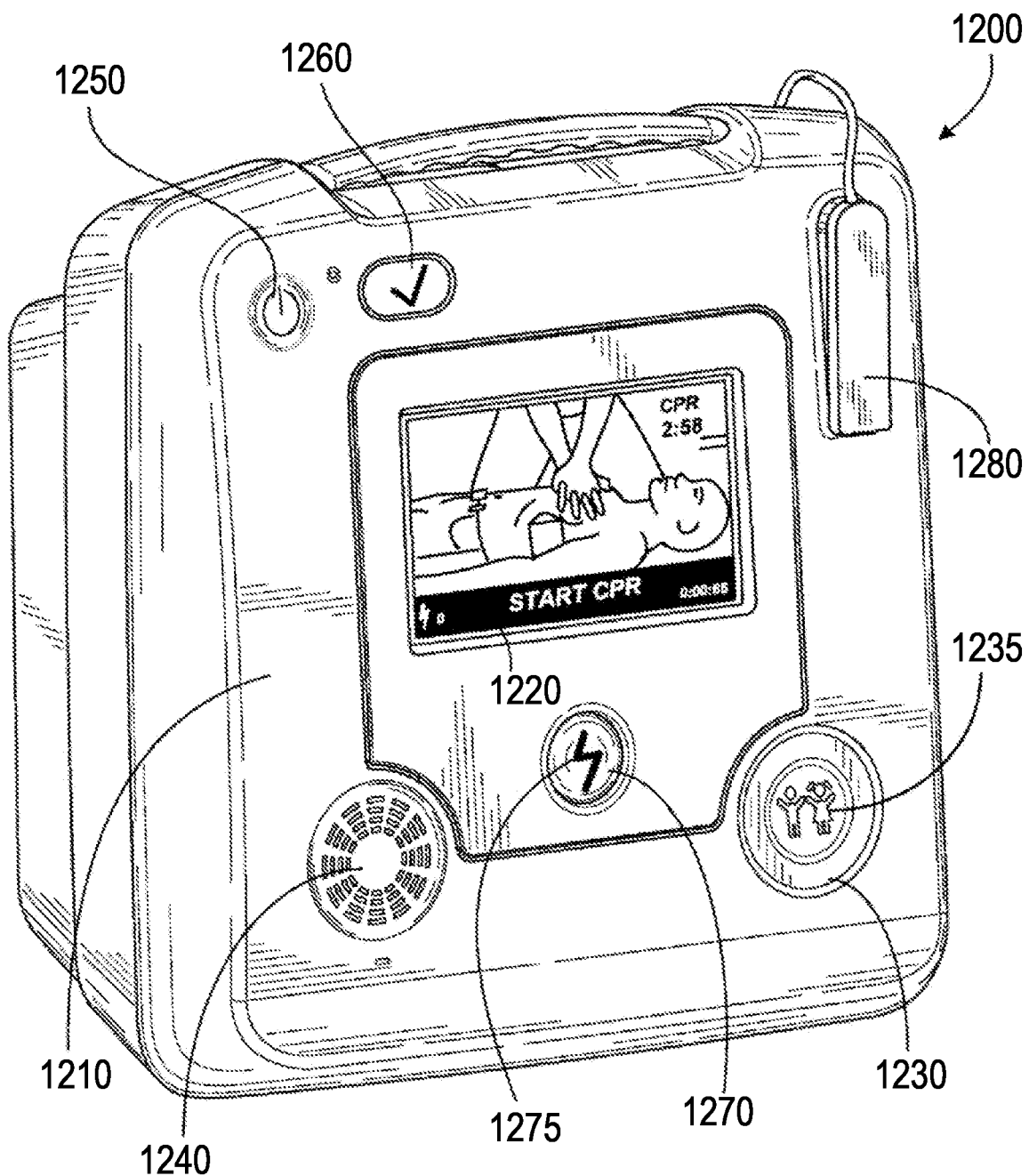
FIG. 12 illustrates an example medical device for aerially deploying to an emergency medical event.

FIG. 12 shows an example of an Automated External Defibrillator (AED) 1200. The AED 1200 has a chassis 1210 which houses and protects the internal components of the AED 1200. The chassis 1210 is constructed to provide one or more inputs and outputs, which may include a user interface. The user interface includes a graphical display 1220 which can display instructions, treatment feedback, and other information to a user which may be useful for administering resuscitative therapy.

The user interface of the AED 1200 has a control 1230 for changing the operating mode of the AED 1200. In some implementations, the control 1230 can switch the operating mode between an adult operating mode and a pediatric operating mode. In some embodiments, the control provides the ability for the AED to switch between adult and pediatric operating modes dynamically during the resuscitation process.

The AED 1200 has an indicator 1235 for providing to the user an indication (e.g., illumination, audible sound, display, etc.) of the current operating mode in use. The AED 1200 includes a speaker 1240. The speaker 1240 can provide auditory instructions and/or other feedback to a user during treatment. The AED 1200 includes a switch 1250 for turning the AED 1200 into an on or off state. The AED 1200 can include a readiness indicator 1260 which reports whether the AED 1200 needs maintenance or other repair such that it is unfit for current use. The AED 1200 can include a control, such as a button or switch, for activating treatment, such as a defibrillating shock. In FIG. 12, for example, the control is a shock button 1270. The AED 1200 includes a port 1280. The port 1280 can receive signals from sensors, for example, regarding one or more physiological parameters of the patient. Such physiological parameters (e.g., ECG signal) may be analyzed by the processor according to an appropriate algorithm to make a determination of whether a defibrillating shock should be administered to the patient. The port 1280 can communicate signals such as a defibrillating shock. For example, a cable leading to defibrillating electrodes can be interfaced with the port 1280.

The internal components of the AED may include a computer processor and one or more capacitors. The capacitors can be charged during use of the AED. The capacitors can be quickly discharged though an external electrode assembly, interfaced with the AED via the port 1280, to provide a therapeutic electric shock. The capacitors can discharge in such a way as to correctly deliver an appropriate electric shock having a desired level of energy (e.g., pre-configuration default set to 120-200 J for an adult patient, 50-85 J for a pediatric patient) to the patient during treatment.

The chassis 1210 of the AED houses and protects the internal components of the AED. The corners of the AED can be rounded, truncated, beveled or otherwise structured so that the chassis 1210 is free of sharp edges and, hence, may be easy and safe for a person to handle. A handle can be attached to the chassis 1210 for the AED to be comfortably and conveniently carried. Various input and output components of the AED can be flush with the chassis exterior such that the exterior has a smooth and sleek feel/appearance. For example, in FIG. 12, the control 1230, speaker 1240, and power button 1250 are seated in the chassis exterior such that they do not protrude outward from the chassis exterior but rather form depressed features relative to the outer casing surface of the chassis. The chassis can be constructed from any suitable material, such as a plastic or other rigid material.

The AED may have a user interface which includes a display 1220. The display 1220 can be a full-color screen, such as a LED-backlit screen. The display 1220 can be covered by a touch-sensitive film or other device such that the display 1220 has touch-screen functionality. The display 1220 can be used to show instructions for treatment, warnings, a status of the AED, or other information which can be relevant to treatment of the patient. In some examples, the display 1220 can show still images of instructions for treatment. In some examples, the display 1220 can show animated instructions for treatment. In some implementations, the display 1220 can show real-time or near real-time feedback, measurements, or both based on signals provided from the electrode assembly or other sensors or inputs of the AED.

FIGS. 13A-13D illustrate front, back, and side views of an example airbag case 1300 mounted to a medical device 1302, such as the medical device 1200 of FIG. 12. The airbag case 1300 includes a number of airbag units 1304a-1304m. The airbag units 1304a-1304m, for example, may be inflatable to substantially surround the airbag case 1300, protecting the medical device 1302 from damage due to impact against any surface of the airbag case 1300. In some embodiments, the airbag units 1304a-1304m are individually detachable and replaceable. For example, the airbag units 1304a-1304m may be selectively inflated based on an anticipated impact orientation. Further to the example, only the inflated and used airbags may require replacement prior to subsequent use of the airbag case 1300. The airbag case, in some implementations, includes a handle opening 1308 where a descender unit or descent line may be attached for controllably dropping the medical device 1302 to the location of a medical emergency.

Figure 13A:
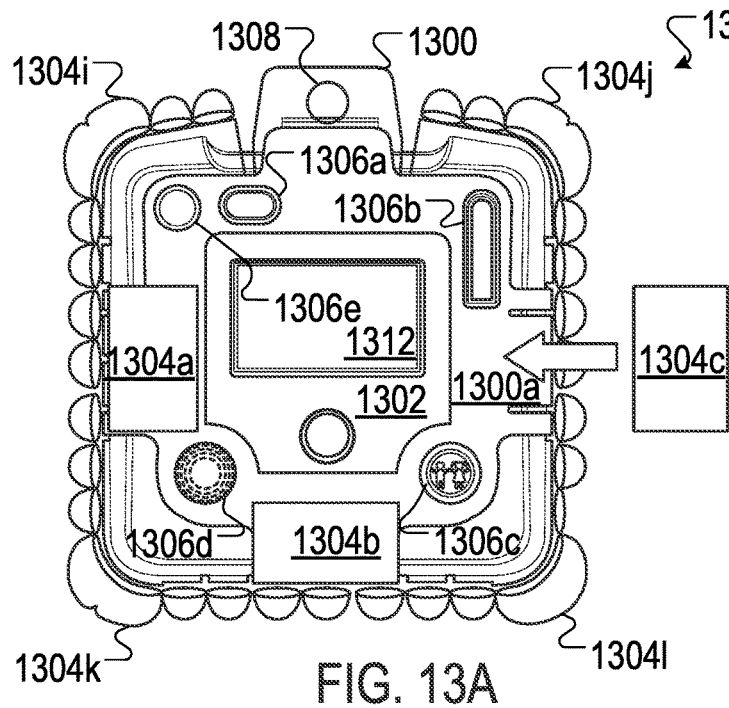
FIGS. 13A-13D illustrate an example airbag case mounted to a medical device.

As illustrated in a front view 1310a of FIG. 13A, front-mounted airbag units 1304a, 1304b, and 1304c, in some implementations, are arranged to enable access to a display region 1312 of the medical device 302 as well as input/output features 1306 of the medical device 1302. A front portion 1300a of the airbag case 1300, for example, may include cut-out regions for enabling access to on/off switch 1250, readiness indicator 1260, sensor port 1280, speaker 1240, and operating mode control 1230, as described in relation to FIG. 12. Upon inflation, in some embodiments, the controls 1304 remain accessible so that, upon landing at the location of the medical emergency, the medical device may be used without removing the medical device from the airbag case 1300.

Figure 13C:
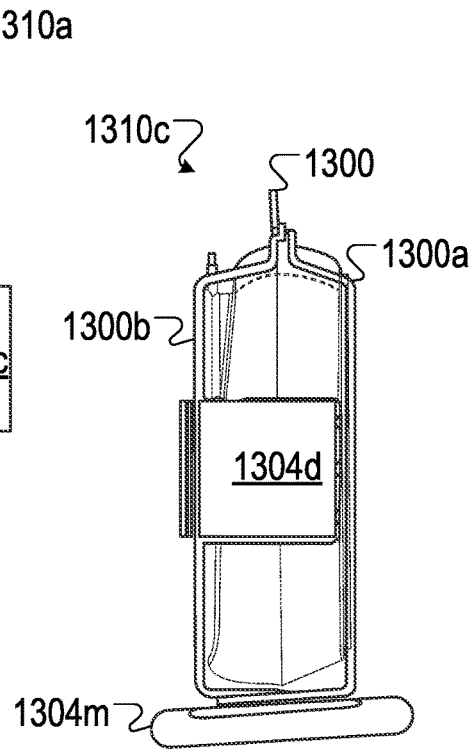
Figure 13B:
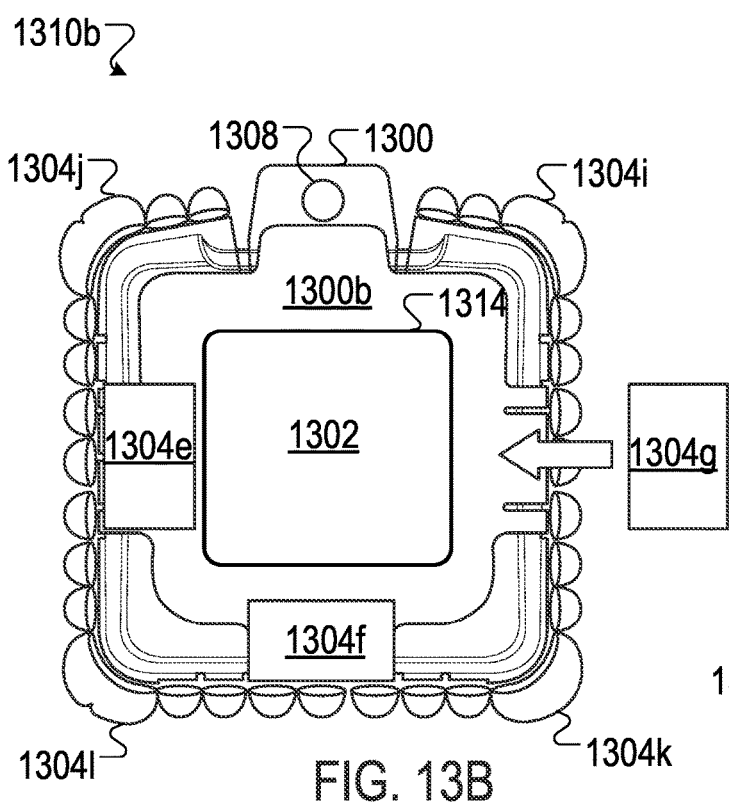

Turning to FIG. 13B, a rear view 1310b of the airbag case 1300 reveals rear-mounted airbag units 1304e, 1304f, 1304g arranged around a cut-out region 1314 providing access to a back side of the medical device 1302. In the example of the AED defibrillator 1200 of FIG. 12, the cut-out region 1314 may be disposed in a manner that provides access to defibrillation electrodes. The cutout-region 1314, for example, may be substantially clear of interference from any of the airbag units 1304 even while the airbag units 1304 are inflated. The defibrillation electrodes, for example, may be quick-releasable from a feature on the rear of the medical device 1302 or otherwise stored beneath the rear portion 1300b of the airbag case 1300 in a manner that allows the electrodes to be drawn away from the airbag case 1300 and deployed for use.

Figure 13D:
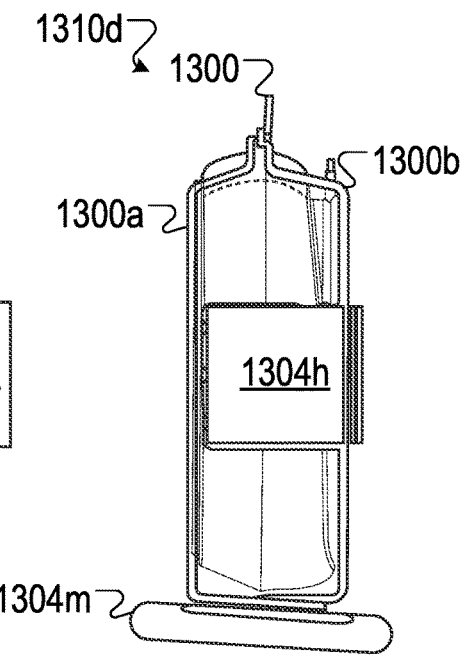

As shown in FIG. 13A and FIG. 13B, in some implementations, corner-mounted airbags 1304i, 1304j, 1304k, and 1304l may be disposed to wrap around the four corners of the airbag case 1300, thereby protecting the airbag case 1300 from damage due to impact with one of the corners of the airbag case 1300. In further embodiments, other airbag units 1304 may be designed as wrap-around units. For example, the airbag unit 1304c may wrap around the side of the airbag case 1300 to the back of the airbag case 1300 as part of the airbag unit 1304e, and the airbag unit 1304b may wrap around the bottom of the airbag case 1300 as part of the airbag unit 1304f. Conversely, as illustrated in FIG. 13C and FIG. 13D, side airbags 1304d and 1304h and bottom airbag 1304m may be provided on the airbag case 1300 for purpose of protecting these side surfaces.

Figure 14A:
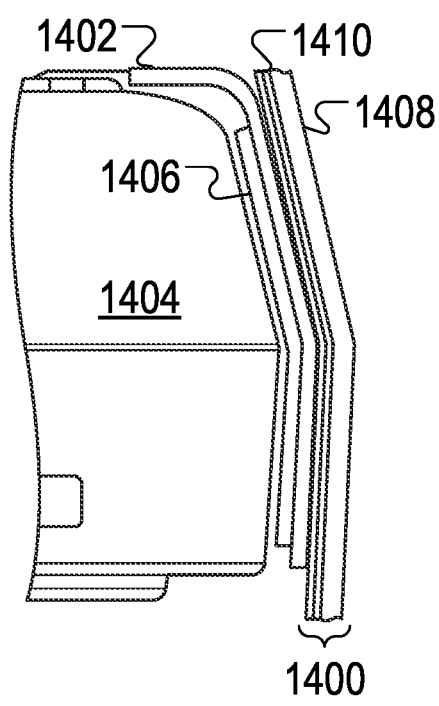
FIGS. 14A and 14B illustrate an example airbag mounted to an airbag case for protecting a medical device from impact forces in a compact state and in an inflated state.
Figure 14B:
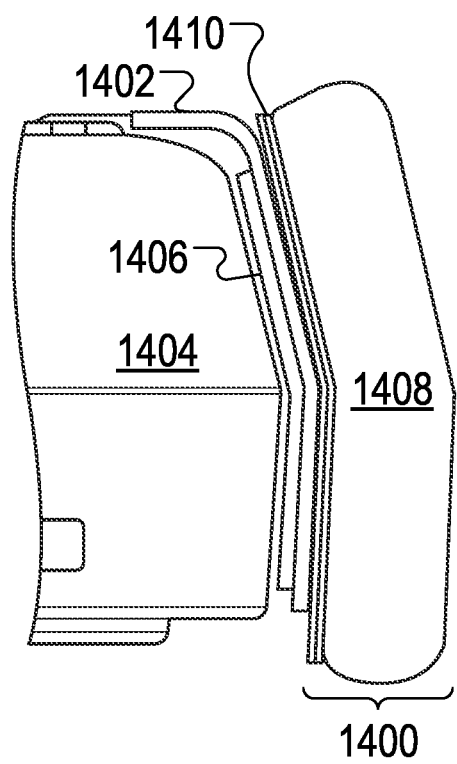

In some implementations, the airbag case 1300 includes inner cushioning for additional protection of the medical device 1302. For example, the airbag case 1300 may include deformable bumpers, a liner, or scratch-resistant material to protect the medical device 1302. In one example, an inner surface of the airbag case 1300 may be substantially covered with a foam layer to provide additional cushioning upon impact. Turning to FIGS. 14A and 14B, an example airbag unit 1400 is mounted to an airbag case 1402 protecting a medical device 1404 from impact forces. The airbag case includes a cushioned layer 1406 for protecting the medical device 1404 from impact forces.

Figure 15A:
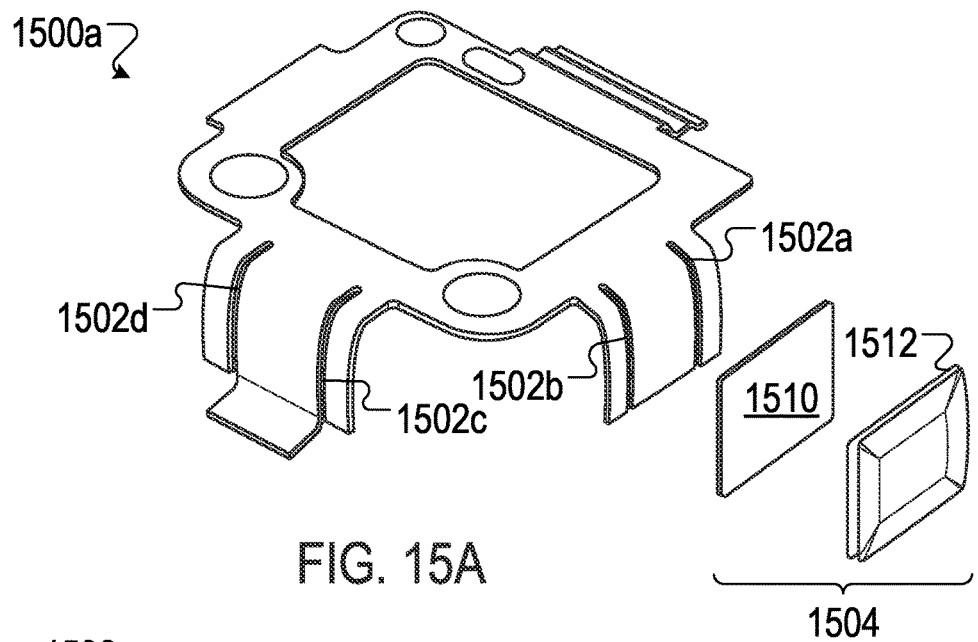
FIG. 15A and FIG. 15B illustrate example case sections of an airbag case for protecting a medical device from impact forces.
Figure 15B:
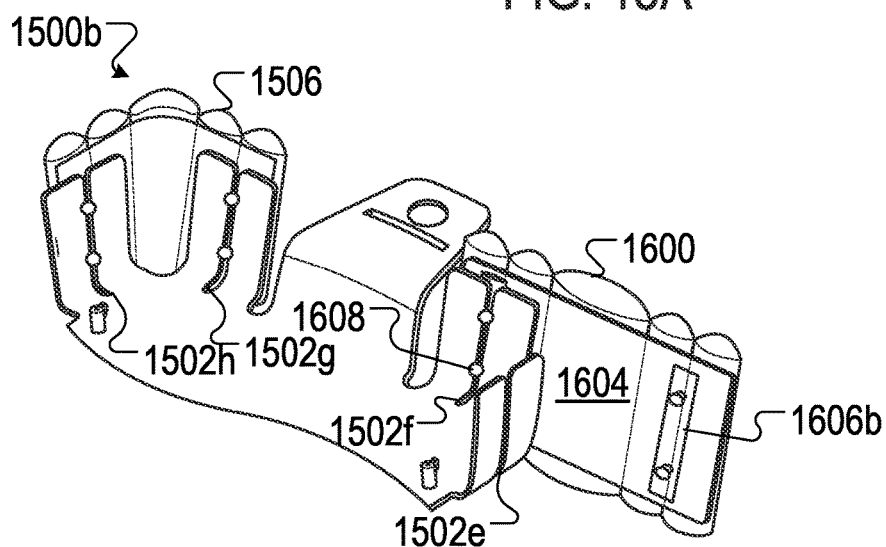

The airbag unit 1400 is illustrated in a compact (uninflated) state in FIG. 14A and in a deployed (inflated) state in FIG. 14B. As is apparent in the illustration in comparing the compact and deployed states, the airbag unit 1400 is composed of an airbag portion 1408 and a mounting portion 1410. Turning to FIG. 15A and FIG. 15B, example case sections 1500a, 1500b of an airbag case 1500 for protecting a medical device from impact forces are illustrated. The airbag case sections 1500a, 1500b include mounting slots 1502a through 1502h for mounting airbag units, such as airbag unit 1504 of FIG. 15A, airbag unit 1506 of FIG. 15B, and an airbag unit 1600 of FIG. 16, illustrated in partially mounted position in FIG. 15B.

Turning to FIG. 15A, airbag unit 1504 includes an airbag 1510 and an airbag mounting substrate 1512. The airbag unit 1504 is aligned for positioning in a side mounting location of the upper portion 1500a of the airbag case 1500, attached to slots 1502a and 1502b. In some implementations, the mounting substrate 1512 is substantially rigid. For example, the mounting substrate 1512 may be composed of plastic, cardboard, plywood, or other lightweight material for securing the airbag unit 1504 to the airbag case 1500. In other implementations, the mounting substrate 1512 is flexible or semi-flexible. For example, the mounting substrate may be composed of a fiber material such as felt, a silicon or rubber, or other lightweight flexible material for securing the airbag unit 1504 to the airbag case 1500.

Figure 16:
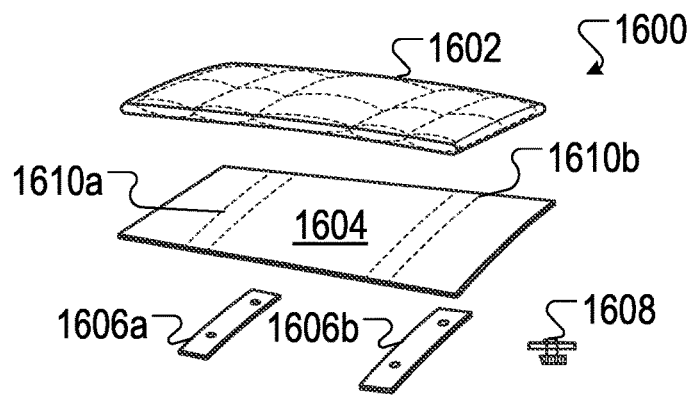
FIG. 16 illustrates an example airbag and mounting mechanism for mounting the airbag to an airbag case for protecting a medical device from impact forces.

As illustrated in FIG. 16, the airbag unit 1600 includes an airbag 1602, a mounting substrate 1604, mounting brackets 1606a and 1606b, and connector 1608. The mounting brackets 1606a and 1606b, for example, may be attached to the substrate at mounting locations 1610a and 1610b, indicated with dotted lines. The connector 1608 is an example of multiple connectors used to mount the airbag unit 1600 to the airbag case 1500. For example, as illustrated, each mounting bracket 1606 includes a set of two openings for securing the airbag unit 1600 to the airbag case 1500.

Returning to FIG. 15B, the airbag unit 1600 of FIG. 16 is illustrated as connecting to a corner mounting position on the lower portion 1500b of the airbag case 1500 by sliding the connectors attached to the mounting brackets 1606 into the slots 1502e and 1502f. When fully mounted, the airbag unit 1600 will wrap around the corner as illustrated in the mounted configuration of airbag unit 1506.

In deploying the airbag units attached to an airbag case, in some implementations, all airbag units are configured to deploy simultaneously. The triggering mechanism may be mechanical and/or electrical in nature. A mechanical trigger, for example, may include ties between a set of airbag units attached to an airbag case configured to be pulled upon deployment. For example, the ties may be pulled by an end of the string or tied-together chain of strings being secured to a surface of an unmanned aerial unit, such as an inner surface of a cargo bay. In an example involving an electrical trigger, the airbag units may be electrically triggered by a contact with one or more of the mounting connectors and an electrical connection in each of the mounting slots.

In some embodiments, the airbag units are selectively deployed based upon a direction of fall of the airbag case. Selective deployment provides the benefit of directing all deployment fluid (e.g., liquid or gas) to a smaller number of airbags. Selective deployment can allow for a smaller amount of gas being carried within or upon the airbag case. Further, selective deployment can allow for re-use of non-deployed airbag units, reducing cost and materials used in delivering medical equipment through dropping the medical equipment to the location of an emergency. The deployment may be electrically and/or mechanically triggered. In an example of an electrical trigger, one or more directional sensors, such as an accelerometer, gyroscope, or magnetometer, may be used to determine a direction of fall. The directional sensor-based trigger may be activated, in some examples, on a number of X signals indicating a same general direction of travel and/or Y amount of time having passed since deployment of the airbag case. Deployment of the airbag case, for example, may be identified based upon an initial indication, by the directional sensor(s), of velocity of the airbag case. This may "arm" a triggering mechanism for deploying the airbags.

In some implementations, the triggering mechanism is a mechanical triggering mechanism having a liquid switch. The liquid switch, for example, may include a liquid component and a gas component, where the liquid moves to a region opposite the direction of fall due to gravitational forces. The liquid, in some examples, can include mercury, oil, or water. Rather than air, in some embodiments, a low-density liquid and a high-density liquid are used to provide the trigger mechanism. The low-density liquid, for example, may include mercury or water, and the high-density liquid may include oil. Airbags positioned opposite a direction of travel of the fluid (e.g., in the direction of the fall) may be triggered. The mechanical triggering mechanism may be activated, for example, based upon an amount of time having passed since deployment of the airbag case.

Figure 17:
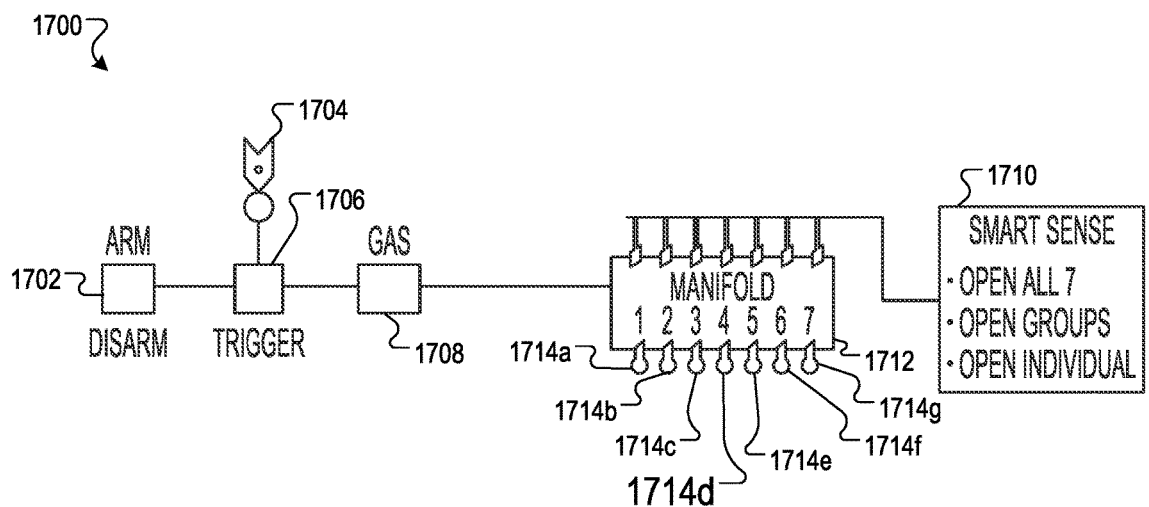
FIG. 17 illustrates a block diagram of an example circuit design for intelligent deployment of airbags of an airbag case for protecting a medical device from impact forces.

FIG. 17 illustrates a block diagram of an example block circuit 1700 for intelligent deployment of airbags of an airbag case for protecting medical equipment from impact forces. As illustrated, the circuit 1700 may initially be armed 1702, for example as described above (e.g., upon releasing or dropping the airbag case containing the medical equipment). Arming the circuit 1700, for example, may initiate monitoring for a signal 1704 that acts as a trigger 1706 for releasing an inflation gas or liquid 1708, such as compressed air. As discussed above, the triggering mechanism may be based upon a length of time since arming of the circuit 1700, a substantially steady state velocity having been reached, and/or a substantially steady orientation having been reached. The trigger signal 1704 may be received from a clock unit, monitoring processor, and/or one or more directional sensors.

In some implementations, the gas 1708 is distributed to the airbag units of the airbag case through a manifold 1712. As illustrated, the manifold 1712 includes a set of seven selectable destinations 1714a through 1714g for the gas 1708.

Figures 18A, 18B:
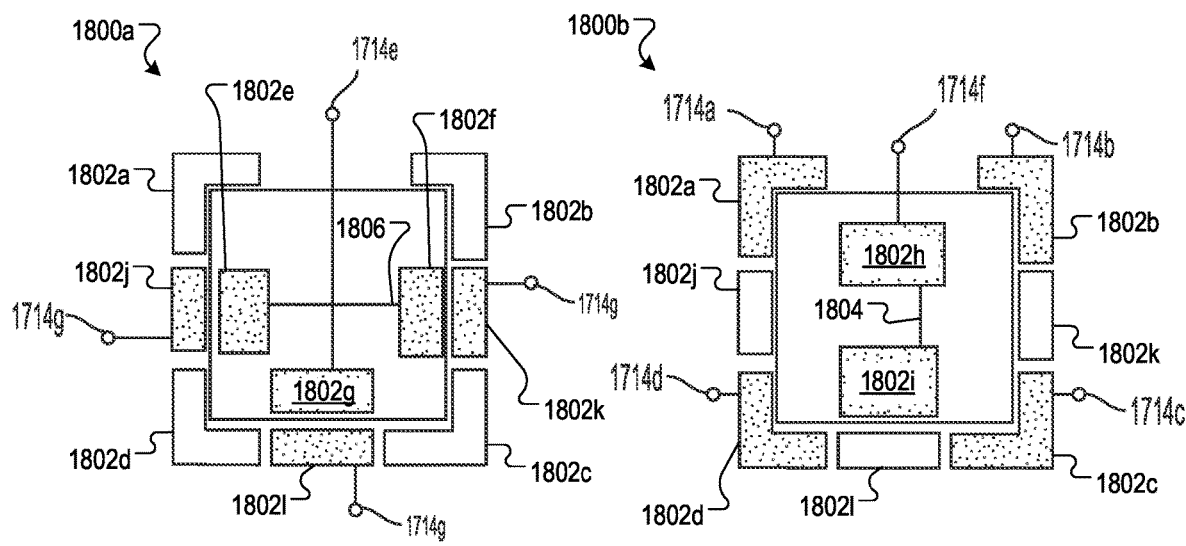
FIG. 18A and FIG. 18B illustrate example positions for gas delivery to airbag units mounted on an airbag case.

FIGS. 18A and 18B illustrate example positions for gas delivery to airbag units 1802 mounted on an airbag case from the manifold 1712 of FIG. 17. FIG. 18A, for example, represents a front side 1800a of an airbag case 1800 and FIG. 18B represents a rear side 1800b of the airbag case. The positions are for purpose of example only. In other embodiments, different numbers of airbag units, positionings of airbag units, and/or inflation groupings of airbag units may be configured. Further, in other embodiments, the manifold 1712 may include fewer or more outputs 1714.

As illustrated in FIG. 18B, in some implementations, corner-mounted airbag units are individually fed by outputs of the manifold 1712. As shown, corner-mounted airbag unit 1802a is fed by manifold output 1714a, corner-mounted airbag unit 1802b is fed by manifold output 1714b, corner-mounted airbag unit 1802c is fed by manifold output 1714c, and corner-mounted airbag unit 1802d is fed by manifold output 1714d.

Returning to FIG. 18A, in some implementations, a set of front-side airbag units 1802e, 1802f, and 1802g are fed by manifold output 1714e. A cross-connection 1806, for example, splits the incoming manifold feed 1714e between the three airbag units 1802e, 1802f, and 1802g. Similarly, As shown in FIG. 18B, a set of rear-side airbag units 1802h and 1802i are fed by manifold output 1714f. As shown, the airbag units 1802h and 1802i are fed in series, with a connection 1804 positioned between airbag unit 1802 and airbag unit 1802i.

In some implementations, as illustrated in FIG. 18A, a set of side-mounted airbag units 1802j and 1802k, along with a bottom-mounted airbag unit 1802l, are fed by manifold output 1714g. The output of manifold output 1714g, for example, may be split in three directions to reach each of the side-mounted airbag units 1802j and 1802k as well as the bottom-mounted airbag units 1802l.

Returning to FIG. 17, the outputs 1714a through 1714g of the manifold 1712 are individually activated, in some implementations, by smart sensing circuitry 1710. In some embodiments, the smart sensing circuitry 1710 is designed to open individual feeds 1714 of the manifold 1712 based upon certain sensed directions of fall of the airbag case. For example, upon determining that the airbag case is traveling with a front surface downward, the manifold feed 1714e may be activated to inflate airbags 1802e, 1802f, and 1802g. The smart sense circuitry 1710, in some embodiments, is designed to open groups of feeds 1714 of the manifold 1712 based upon certain sensed directions of fall of the airbag case. For example, the smart sense circuitry 1710, based on sensing that the airbag case is traveling in a manner that a bottom corner is likely to initially contact the ground, may activate inflation of feed 1714c to the particular corner airbag unit 1802c as well as manifold feed 1714g for inflating side airbag units 1802k and 1802i surrounding corner 1802c. In some embodiments, the smart sensing circuitry 1710 is configured, based on certain events, to activate all gas feeds 1714 of the manifold 1712. In some examples, if the smart sensing circuitry 1710 enters a failure state (e.g., one or more sensors not functional) or does not determine a likely contact position within a threshold period of time, the smart sensing circuitry 1710 may default to inflating all airbag units 1802.

As discussed above, the smart sensing circuitry 1710 may include electrical and/or mechanical mechanisms for anticipating a point of impact upon the airbag case. One or more directional sensors, distance sensors, airflow sensors, or other mechanisms may provide indication of an orientation of the airbag case while dropping to a location. The smart sensing circuitry 1710, in some embodiments, receives at least a portion of the sensor data from one or more sensors of the medical equipment, such as a gyroscope built into a medical device. In some embodiments, the airbag case includes at least a portion of the sensors. Further, a timing mechanism may be used to sample sensor outputs and/or to activate trigger (e.g., as a default to failing to determine a likely impact orientation). The smart sense circuitry may include decision logic to estimate the impact orientation based on sensor inputs. The decision logic may include a processor executing a set of instructions and/or hardware logic circuitry programmed into and/or designed as one or more logic circuits. For example, the decision logic may include a central processing unit (CPU), graphical processing unit (GPU), field-programmable gate array (FPGA), application-specific integrated circuit (ASIC), and/or other hardware logic functioning with or without software input. The decision logic of the smart sense circuitry may be configured at least in part as part of the medical equipment. For example, the medical device may be designed to provide signals for activating feeds 1714 of the manifold 1712.

Figure 19A:
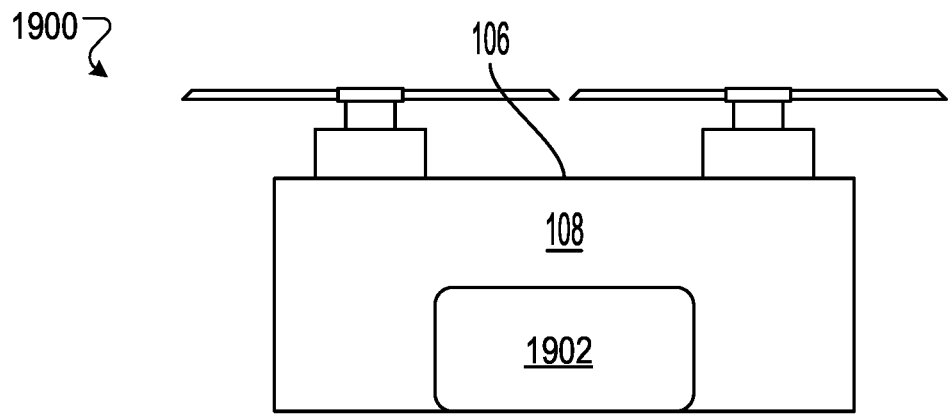
FIG. 19A and FIG. 19B illustrate an example drop sequence for dropping a medical device to the location of an emergency medical event.
Figure 19B:
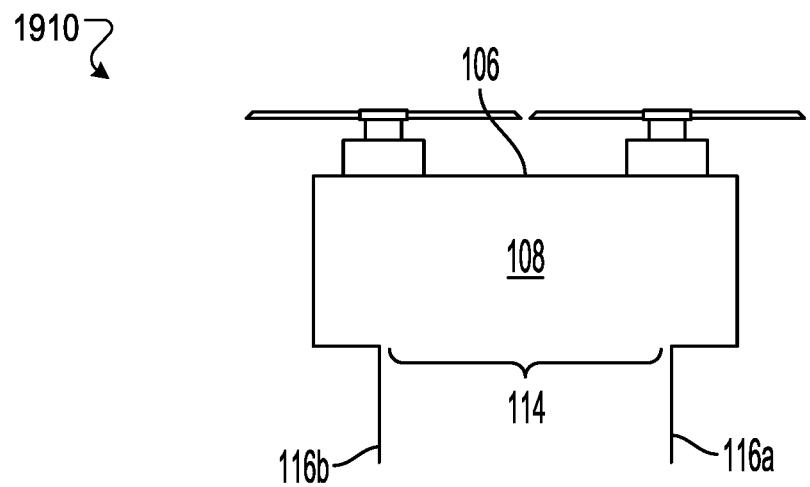
Figure 19B:
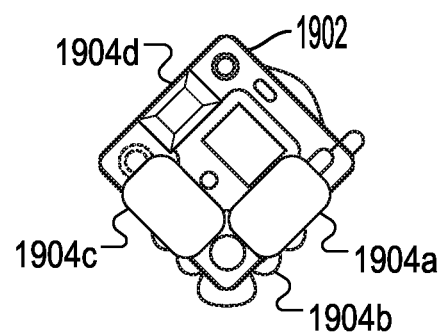

FIG. 19A and FIG. 19B illustrate an example drop sequence 1900 and 1910 for dropping a medical device 1902 to the location of an emergency medical event. As illustrated in FIG. 19A, the medical device 1902 is disposed in a cargo hold 108 of an unmanned aerial vehicle 106. Turning to FIG. 19B, when the unmanned aerial vehicle 106 has reached its destination above the location, cargo doors 116*a* and 116*b* are opened, and the medical device 1902 drops from the opening 114.

In some implementations, as the medical device 1902 falls to the location, a portion of a set of airbags 1904 coupled to the medical device 1902 deploy to cushion the fall and thereby protect the medical device 1902 from damage due to impact forces. As illustrated a right airbag 1904*a*, a corner airbag 1904*b*, and a lower airbag 1904*c* are inflated. A left side airbag 1904*d* is uninflated. As described above, decision logic may determine which airbags of the set of airbags to inflate. In other implementations, all airbags 1904 may be inflated.

Figure 20:
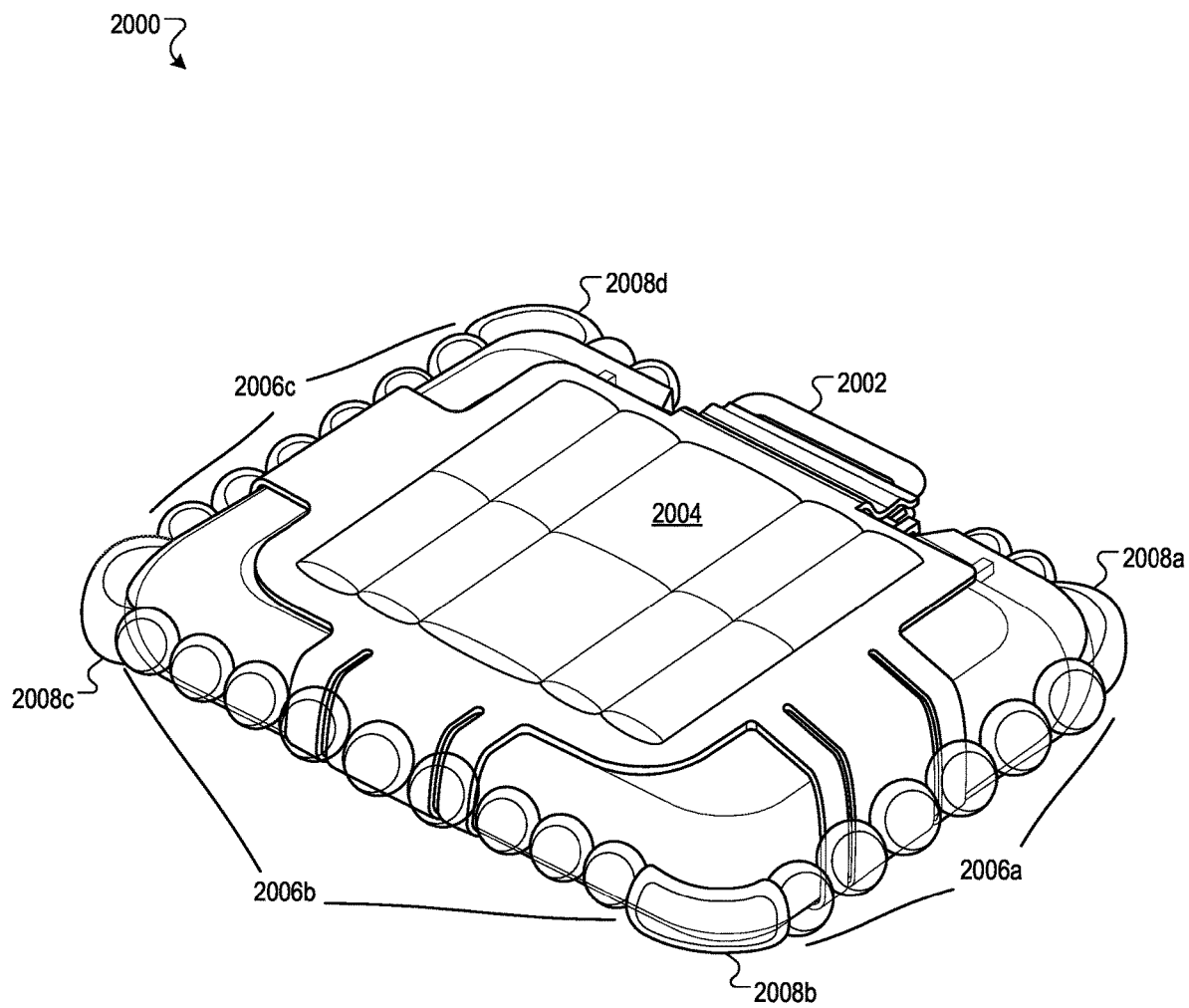
FIG. 20 illustrates a second example airbag case for protecting a medical equipment deployment unit from impact forces.

FIG. 20 illustrates a second example airbag case 2000 for protecting a medical equipment deployment unit 2002 from impact forces. The medical equipment deployment unit, for example, may include a variety of medical equipment packaged in a carrying luggage, such as the suitcase-style medical device 102 depicted in FIG. 2A through FIG. 2D. In other examples, the carrying luggage may include a backpack, duffel bag, or other enclosure for bundling and protecting a variety of medical equipment. In the example of a trauma kit encased in a suitcase or other bag, the medical implements within may include an assortment of tools for triaging a patient, such as bandages, dressings, tourniquets, gauze, instant cold packs, medical tape, pain killers, a blanket, sheers, protective gloves, burn cream, topical antibiotic, antiseptic, saline, protective mask and/or face shield, and a first aid manual. The trauma kit may further include a communication device for obtaining assistance from remote medical personnel, such as a tablet computer, cellular phone, smart phone, satellite phone, or walkie-talkie. In some implementations, the medical equipment deployment unit includes multiple medical devices bundled within the case 2000. For example, the trauma kit suitcase may be bundled with a portable AED device, a portable ventilator device, and/or a communication device for obtaining assistance from remote medical personnel.

As illustrated, the airbag case 2000 includes a top airbag 2004, side airbags 2006*a*, 2006*b*, and 2006*c*, and corner airbags 2008*a*, 2008*b*, 2008*c*, and 2008*d*. The airbag case 2000 may also include a bottom airbag (not illustrated). The airbags 2004, 2006, and 2008, in some implementations, are all inflated based upon a trigger. In other implementations, certain airbags 2004, 2006, and 2008 are inflated, for example based on an orientation of the medical equipment deployment unit upon being dropped (e.g., from an unmanned aerial vehicle).

Figure 21:
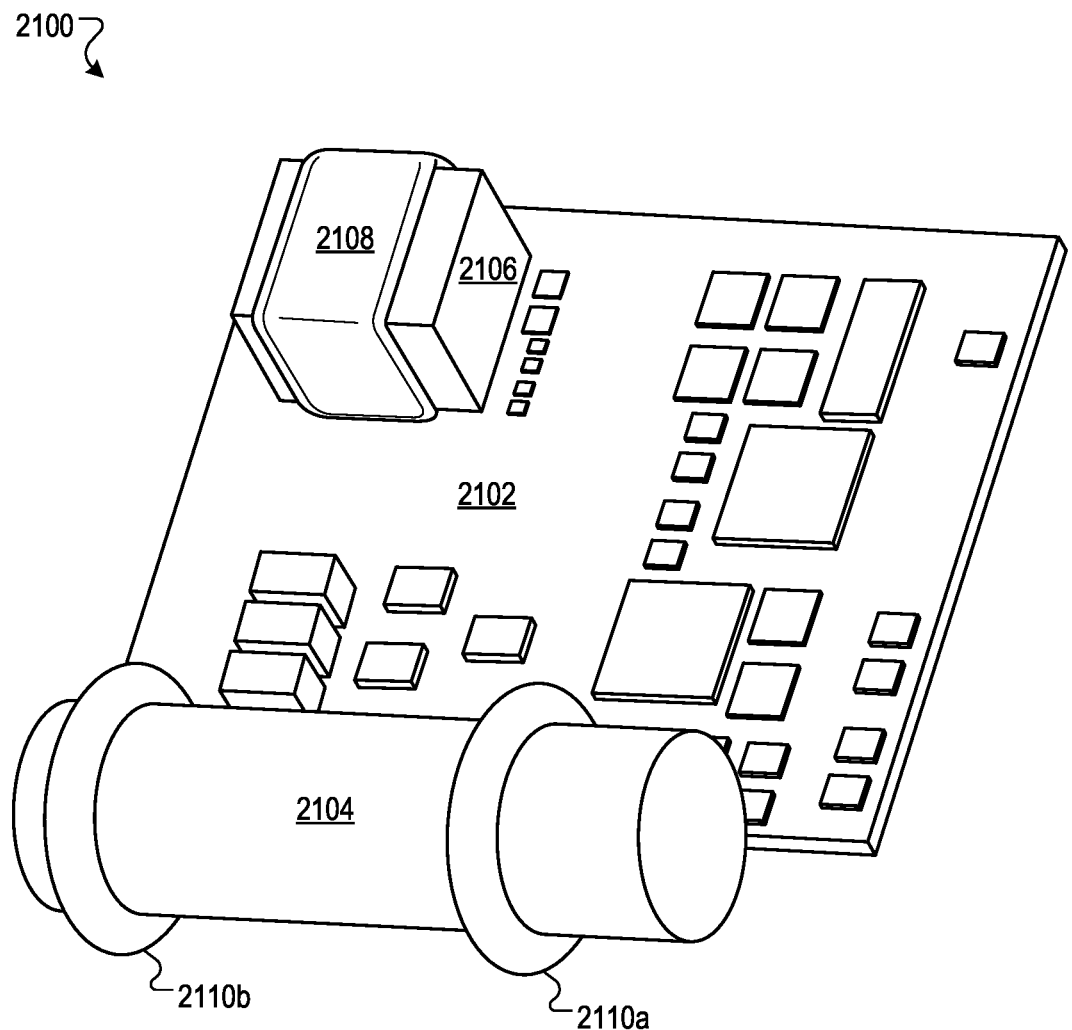
FIG. 21 is a block diagram of an example internal circuit design for a defibrillator medical device.

FIG. 21 is a block diagram of an example internal circuit design 2100 for a defibrillator medical device. The circuit design 2100 includes a circuit board 2102 having a variety of electronic components. The electronic components, for example, include a capacitor 2104 to produce a defibrillation shock and a communication module 2106 for communicating with a separate computing device. The communication module 2106, for example, may be a wireless communication unit for communicating via Wi-Fi or Bluetooth.

Each of the capacitor 2104 and the communication module 2106 extend above a surface of the circuit board 2102 and other electronic components attached thereto. In some implementations, to avoid damage to these elevated components, for example due to force of impact with a housing of the medical device, inflatable protection elements 2108, 2110*a*, and/or 2110*b* may be inflated to cushion and secure the electronic components 2104 and/or 2106. The inflatable protection elements 2108, 2110*a*, and/or 2110*b*, for example, may be inflated upon control circuitry of the circuit board 2102 detecting a threshold g-force acting upon the medical device. Inflation of the inflatable protection elements 2108, 2110*a*, and/or 2110*b* may be accomplished, in some examples, through igniting a propellant or releasing a compressed gas such as carbon dioxide.

In some implementations, the inflatable protection elements 2108, 2110*a*, and/or 2110*b* are controllably deflatable upon detection of a second, lower, threshold g-force acting upon the medical device. The second threshold g-force may be zero g-force or lack of detectable g-force. The inflatable protection elements 2108, 2110*a*, and/or 2110*b* may be deflatable, for example, to allow for greater air flow around components of the circuit board 2102 and thus greater cooling of the electrical components.

As illustrated, in some embodiments, the capacitor 2104 is protected by doughnut-shaped or toroidal inflatable protection elements 2110*a* and 2110*b* at least partially encircling a diameter of the capacitor 2104. In other embodiments, more or fewer inflatable protection elements 2110 may be used. Rather than encircling the capacitor 2104, in other embodiments, the capacitor 2104 may be protected length-wise by one or more inflatable protection elements. The inflatable protection elements may be mounted, in some examples, against a housing of the medical device, along an edge of the circuit board 2102, and/or along one or more surfaces of the capacitor 2104.

Turning to the communication module 2106, in some embodiments, a wrap-around inflatable protection element 2108 may protect multiple sides of the communication module 2106 (e.g., including one or more sides facing walls of a housing of the medical device). In other implementations, the communication module 2106 is similarly encircled with a toroidal inflatable protection element such as the inflatable protection elements 2110*a* and 2110*b*.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. An apparatus for limiting force of impact on a medical device dropped to a location of an emergency medical event, the apparatus comprising:
   an external case at least partially surrounding or integrated with the medical device; and
   a plurality of impact dampening elements coupled to the external case, the plurality of impact dampening elements being configured to transform from a deflated state to an inflated state while the medical device is dropped to the location, wherein
      in the deflated state, the plurality of impact dampening elements is in a compact form, and
      in the inflated state, the plurality of impact dampening elements expands to buffer the force acting on the medical device upon impact at the location,
   wherein transforming from the deflated state to the inflated state comprises
      analyzing one or more sensor signals to identify a downward pointing side of the external case, and
      selectively inflating a portion of the plurality of impact dampening elements corresponding to a downward pointing side of the external case.

2. The apparatus of claim 1, wherein:
   when in the compact form, the plurality of impact dampening elements is configured to add less than one centimeter to each side of at least one side of the external case; and
   when in the inflated state, the plurality of impact dampening elements expand to add at least 5 centimeters to each side of at least one side of the external case.

3. The apparatus of claim 1, wherein each impact dampening element of the plurality of impact dampening elements is releasably coupled to the external case by at least one quick release connector.

4. The apparatus of claim 1, wherein the external case is a housing of the medical device.

5. The apparatus of claim 1, wherein the external case comprises flexible material surrounding the medical device and secured to the medical device with at least one closure element designed for quick removal of the external case at the location of the emergency medical event.

6. The apparatus of claim 1, wherein the external case comprises rigid material surrounding the medical device and secured to the medical device with at least one closure element designed for quick removal of the external case at the location of the emergency medical event.

7. The apparatus of claim 1, wherein the plurality of impact dampening elements comprises an airbag.

8. The apparatus of claim 1, wherein transforming from the deflated state to the inflated state comprises holding, when dropping the medical device to the location, a pull cord configured to activate inflation of the plurality of impact dampening elements and to release from the external case when pulled.

9. The apparatus of claim 8, wherein:
   the apparatus is designed for being dropped to the location by an aerial delivery vehicle; and
   holding the pull cord comprises securing the pull cord to a surface of a payload region of the aerial delivery vehicle such that the pull cord is held within the aerial delivery vehicle.

10. The apparatus of claim 1, wherein transforming from the deflated state to the inflated state comprises activating inflation through a signal delivered by processing circuitry.

11. The apparatus of claim 10, wherein the processing circuitry is configured to:
    monitor sensor signals indicative of gravitational force (g-force); and
    responsive to detecting at least a threshold g-force, activate inflation of the portion of the plurality of impact dampening elements.

12. The apparatus of claim 10, wherein the medical device comprises the processing circuitry.

13. The apparatus of claim 12, wherein selectively inflating comprises opening an inflation valve responsive to detecting flow direction of a liquid switch mechanism.

14. The apparatus of claim 13, wherein the medical device comprises the liquid switch mechanism.

15. The apparatus of claim 14, wherein the liquid switch mechanism is disposed between the external case and an internal housing of the medical device.

16. The apparatus of claim 13, wherein the liquid switch mechanism comprises a low-density liquid portion and a high-density liquid portion configured to remain separated from the low- density liquid portion.

17. The apparatus of claim 1, wherein a majority of the plurality of impact dampening elements are disposed on a side of the external case corresponding to a heaviest side of the medical device.

18. The apparatus of claim 1, wherein a majority of the plurality of impact dampening elements are disposed on a side of the external case closest to one or more components of the medical device having a lowest impact rating.

19. The apparatus of claim 1, wherein a majority of the plurality of impact dampening elements are disposed on a side of the external case corresponding to a direction of impact force likely to loosen or dislodge one or more components of the medical device.

20. The apparatus of claim 1, wherein the plurality of impact dampening elements are configured to limit a force of impact on the medical device dropped from a height of about 10 feet to no more than 2 g-force impact upon landing on the plurality of impact dampening elements.

21. The apparatus of claim 1, wherein the medical device is an Automated External Defibrillator (AED).

22. The apparatus of claim 1, wherein the external case comprises:
    a three-dimensional shell comprising
       at least two sections, wherein a first section of the at least two sections is at least partially releasable from a second section of the at least two sections for positioning medical equipment in the three-dimensional shell, and
       a plurality of openings for accessing a plurality of input/output features of the medical device while the medical device is enclosed in the three-dimensional shell; and
    a plurality of airbag units comprising
       a first portion of airbag units disposed on a first section of the three-dimensional shell, and a second portion of airbag units disposed on a second section of the three-dimensional shell,
wherein the plurality of airbag units are arranged upon the three-dimensional shell such that the input/output features remain accessible while all airbag units of the plurality of airbag units are in an inflated state.

23. The apparatus of claim 22, wherein the three-dimensional shell comprises a viewing area for viewing a display of the medical device while the medical device is enclosed in the three-dimensional shell.

24. The apparatus of claim 22, wherein the medical device and a second equipment are positioned in the three-dimensional shell.

25. The apparatus of claim 24, wherein the second equipment is a trauma kit.

26. The apparatus of claim 24, wherein the second equipment is a communication device for communicating with remote medical personnel.

27. An apparatus for limiting force of impact on a medical device dropped to a location of an emergency medical event, the apparatus comprising:
    an external case at least partially surrounding or integrated with the medical device;
    a plurality of impact dampening elements coupled to the external case, the plurality of impact dampening elements being configured to transform from a deflated state to an inflated state while the medical device is dropped to the location, wherein
        in the deflated state, plurality of impact dampening elements are in a compact form, and
        in the inflated state, the plurality of impact dampening elements expand to buffer the force acting on the medical device upon impact at the location; and
    a pull cord configured to activate inflation of the at least one impact dampening element and to release from the external case when pulled, wherein
        transforming the at least one impact dampening element from the deflated state to the inflated state comprises
            holding the pull cord when dropping the medical device to the location,
            analyzing one or more sensor signals to identify a downward pointing side of the external case, and
            selectively inflating a portion of the plurality of impact dampening elements corresponding to a downward pointing side of the external case.

28. The apparatus of claim 1, wherein the one or more sensor signals are provided by a sensor built into the medical device.

29. The apparatus of claim 27, wherein:
the apparatus is designed for being dropped to the location by an aerial delivery vehicle; and
holding the pull cord comprises securing the pull cord to a surface of a payload region of the aerial delivery vehicle such that the pull cord is held within the aerial delivery vehicle.

30. The apparatus of claim 27, wherein the at least one impact dampening element is configured to limit a force of impact on the medical device dropped from a height of about 10 feet to no more than 2 g-force impact upon landing on the at least one impact dampening element.

31. The apparatus of claim 27, wherein the external case comprises flexible material surrounding the medical device and secured to the medical device with at least one closure element designed for quick removal of the external case at the location of the emergency medical event.

* * * * *